United States Patent
Coniglione et al.

(12) 
(10) Patent No.: US 6,589,502 B1
(45) Date of Patent: Jul. 8, 2003

(54) RADIOISOTOPE DISPERSED IN A MATRIX FOR BRACHYTHERAPY

(75) Inventors: Roy Coniglione, Duluth, GA (US); John L. Russell, Jr., Alpharetta, GA (US)

(73) Assignee: International Brachytherapy s.a., Seneffe (BE)

(*) Notice: Subject to any disclaimer, the term of this patent is extended or adjusted under 35 U.S.C. 154(b) by 0 days.

(21) Appl. No.: 08/563,087

(22) Filed: Nov. 27, 1995

(51) Int. Cl.[7] ............................................... A61K 51/00
(52) U.S. Cl. .............................. 424/1.25; 600/3; 600/7; 600/8; 424/1.29; 424/1.33
(58) Field of Search ............................... 424/1.11, 1.25, 424/1.29, 1.33; 128/659; 600/3, 4, 5, 6, 7

(56) References Cited

U.S. PATENT DOCUMENTS

| | | | | |
|---|---|---|---|---|
| 3,351,049 A | | 11/1967 | Lawrence | 128/1.2 |
| 4,323,055 A | | 4/1982 | Kubiatowicz | 128/1.2 |
| 4,697,575 A | | 10/1987 | Horowitz | 128/1.2 |
| 4,702,228 A | | 10/1987 | Russell et al. | 128/1.2 |
| 4,754,745 A | | 7/1988 | Horowitz | 128/1.2 |
| 4,763,642 A | | 8/1988 | Horowitz | 128/1.2 |
| 4,784,116 A | | 11/1988 | Russell et al. | 128/1.2 |
| 4,789,501 A | | 12/1988 | Day et al. | 252/645 |
| 4,815,449 A | | 3/1989 | Horowitz | 600/7 |
| 4,849,208 A | * | 7/1989 | Stavrianopoulos | 424/1.1 |
| 4,889,707 A | | 12/1989 | Day et al. | 424/1.1 |
| 4,891,165 A | | 1/1990 | Suthanthiran | 252/633 |
| 4,946,435 A | * | 8/1990 | Suthanthiran et al. | 600/3 |
| 4,994,013 A | | 2/1991 | Suthanthiran | 600/8 |
| 5,011,677 A | | 4/1991 | Day et al. | 424/1.1 |
| 5,011,797 A | | 4/1991 | Day et al. | 501/33 |
| 5,030,195 A | | 7/1991 | Nardi | 600/7 |
| 5,141,487 A | | 8/1992 | Liprie | 600/7 |
| 5,163,896 A | * | 11/1992 | Suthanthiran et al. | 600/8 |
| 5,199,939 A | | 4/1993 | Dake | 600/3 |
| 5,342,283 A | | 8/1994 | Good | 600/8 |
| 5,354,257 A | | 10/1994 | Roubin | 600/7 |
| 5,395,300 A | | 3/1995 | Liprie | 600/3 |
| 5,405,309 A | | 4/1995 | Carden | 600/3 |
| 5,516,881 A | * | 5/1996 | Lee et al. | 528/320 |

* cited by examiner

Primary Examiner—Michael G. Hartley
(74) Attorney, Agent, or Firm—Elman Technology Law, P.C.; Gerry J. Elman

(57) ABSTRACT

Therapeutic sources for use in the practice of brachytherapy are fabricated from radioactive composites of a radioactive powder of palladium-103, yttrium-90, phosphorus-32 or gold-198 and a biocompatible polymeric matrix. The particles of radioactive powder are dispersed within the polymer essentially randomly throughout a particular volume. The polymeric matrix is desirably manufactured with preselected flexibility suitable to its intended use, e.g. in the form of a rod, hollow rod, suture, film, sheet, or microspheroidal particles. The radioactive composites produce therapeutic sources which generate a radiation field that is substantially uniform in all directions. The therapeutic source may assembled from the radioactive composite during a medical procedure to emit the desired amount of therapeutic radiation. Optionally, the polymer is selected to dissolve or degrade in the body at a predetermined rate, the rate chosen depending upon the half life of the radioisotope used in the therapeutic source.

36 Claims, 11 Drawing Sheets

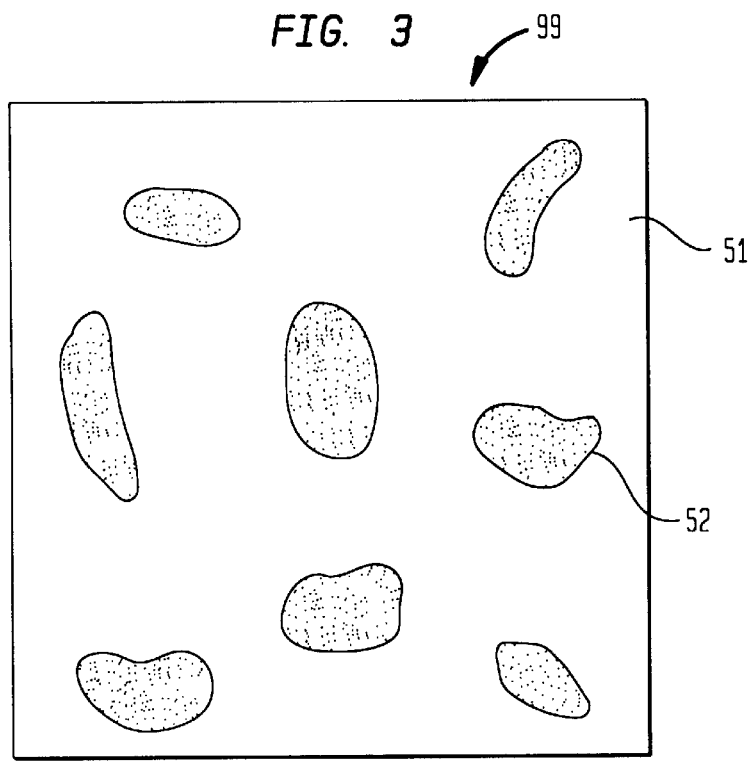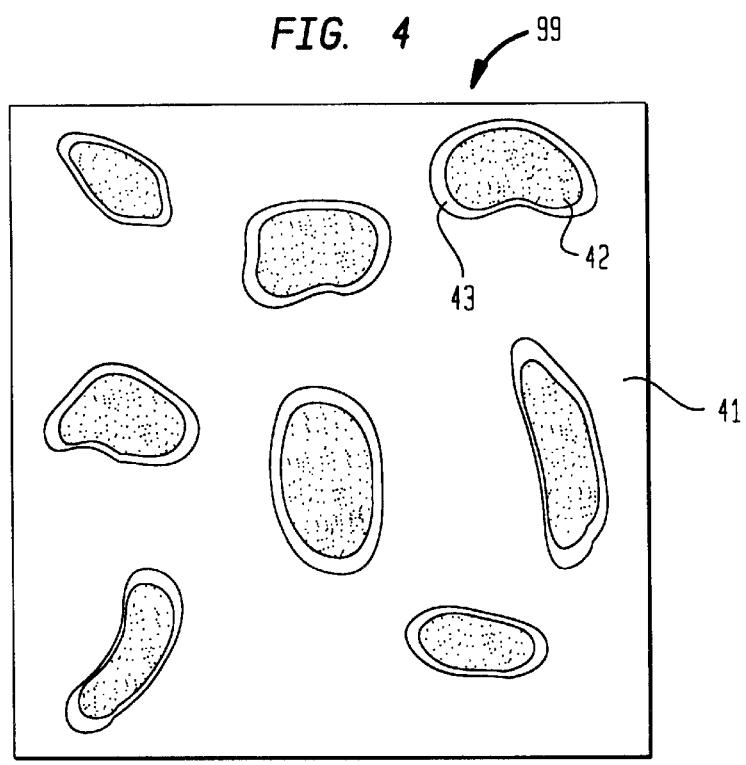

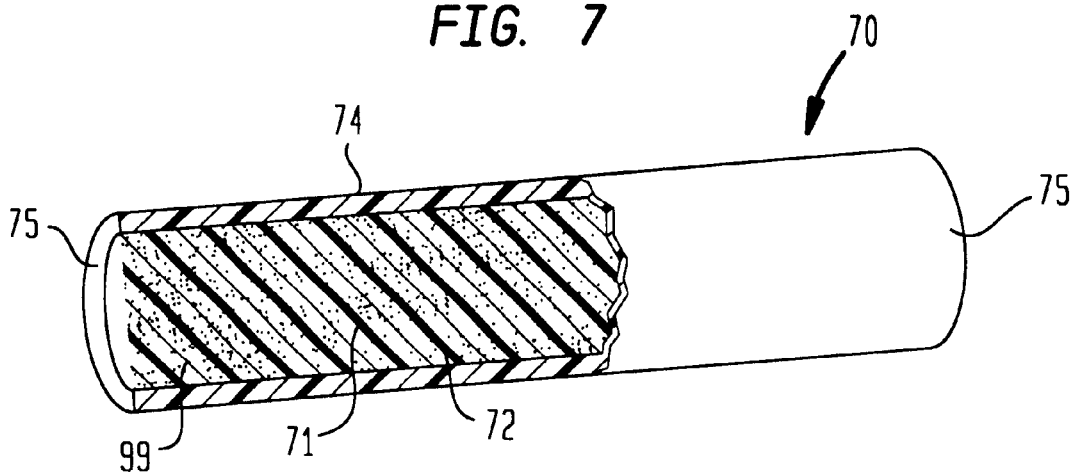
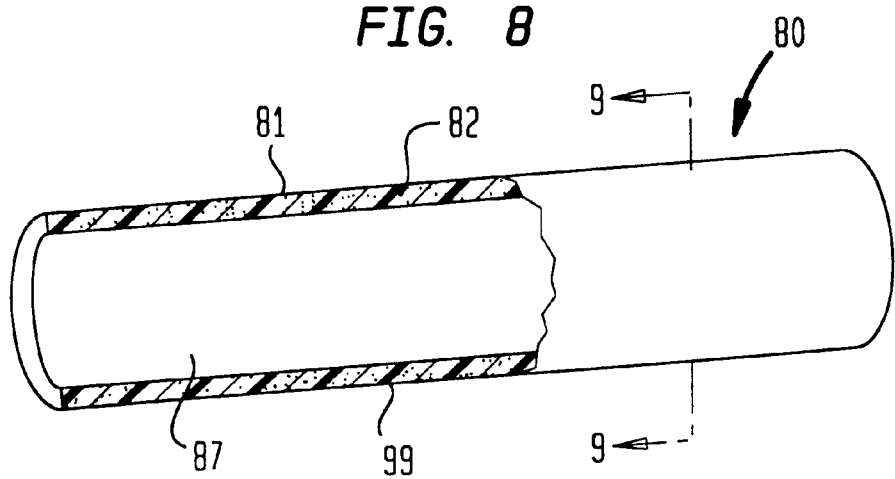

RADIOISOTOPE DISPERSED IN A MATRIX FOR BRACHYTHERAPY

FIELD OF THE INVENTION

The present invention relates to therapeutic radiology. More particularly, the present invention is directed to radioactive materials contained in polymers for use in therapeutic applications known as brachytherapy, to structures fabricated of those materials, and to methods of manufacture and use of these fabricated structures.

BACKGROUND OF THE INVENTION

The local treatment of tissue by exposure to radiation-emitting material is now well established. Such treatment targets the tissue adjacent to the source while keeping the radiation effects on neighboring healthy tissue to a minimum. A major advantage of this form of treatment is that it concentrates the emitted radiation at the site where the treatment is needed, e.g. within a tumor, while keeping the amount of radiation transmitted to the healthy tissue far below what it otherwise would be if the radiation were beamed into the body from an external source, using teletherapy.

Radiation therapy implemented by placing a radiation source near or within the tissue to be treated, ie., brachytherapy, is normally practiced in one of three ways: 1) by placing the source(s) within the tissue to be treated, i.e. interstitial therapy, 2) by placing the source(s) inside a body cavity, normally in association with a positioning device called an applicator, to irradiate tissue surrounding the cavity, i.e., intracavitary therapy, or 3) by placing the source (s) within a vessel or duct, normally in association with a catheter, to treat tissue surrounding the vessel or duct, i.e. intralumenal therapy.

A short segment of gold wire, generally called a "gold grain," containing radiation-emitting gold isotopes such as gold-198, has been found to be a suitable implantable radioactive material. The advantage of using gold grains for interstitial implantation is that gold is compatible with the body. That is, gold neither degrades, dissolves, nor causes any toxic reaction within the body. Radon-222 encapsulated in platinum or other biocompatible metals has also been used in an implantable therapeutic device.

However, materials such as gold-198 and radon-222 have significant counter-indicating characteristics for interstitial tumor treatment in that they emit relatively penetrating radiation, such as high energy gamma radiation. Such high energy radiation not only subjects the patient's healthy tissue to more radiation than is desired, but in addition exposes medical personnel as well as other persons coming into contact with the patient, to significant doses of potentially harmful radiation. Therefore, it is often preferred to use radiation sources which emit lower energy radiation, such as those that emit low energy X-rays, or beta particles.

The use of capsules enclosing the radioactive material is necessary to contain the radioactive material, preventing it from becoming systemically distributed within the patient or escaping into the environment where it could contaminate medical personnel, medical facilities or the general environment. With the exception of gold grains cited above, such encapsulated radioactive material is referred to as "sources" or "seeds."

The construction of the capsule should preferably allow the rapid and facile insertion of the seed into the organ or body part being treated, with minimal trauma to the surrounding tissue. Due to the small size of the capsules, which frequently have outer diameters of the order of 0.5 mm to 0.8 mm, and lengths of the order of 5 mm, a popular technique for implanting the seeds is to insert them into the body percutaneously using a hollow needle which is preloaded with the desired number of seeds and when the needle is in the desired location in the tissue, a stylet is used to hold the seeds in place while the needle is withdrawn from around them, leaving the seeds in the desired location. The use of such small radiation sources is a common way of practicing interstitial brachytherapy.

U.S. Pat. No. 3,351,049 describes seeds with an encapsulating outer shell containing the radiation-emitting isotope, iodine-125. Iodine-125 has a radiation spectrum that is favorable for interstitial use. The encapsulating shell localizes the radioactive iodine to the tumor treatment site by physically preventing the iodine-125 from migrating to other parts of the body. In particular, this technique protects the thyroid, a site of specific iodine uptake. Therefore, encapsulating an isotope permits the use of isotopes that would otherwise dissolve in the body and/or present potential toxic consequences to the patient. Physicians have employed capsules containing radiation-emitting iodine-125 as part of the treatment of patients with tumors.

U.S. Pat. Nos. 4,702,228 and 5,405,309 describe encapsulated seeds containing palladium-103 as the radioactive isotope. Palladium-103 is a radiation source possessing both a preferred radiation spectrum for therapeutic use and a preferred half-life. Palladium metal is insoluble in body fluids and has been injected as a powder directly into living tissue with no reported deleterious effects. Physicians also have used capsules containing palladium-103 for treating patients with tumors. The entire disclosure of each reference cited hereinabove and below is incorporated by reference.

Brachytherapy has met with increasing success over the past decade, in part due to the availability of more appropriate isotopes such as iodine-125 and palladium-103, and in part due to the recognition of the importance of placement of the seeds within the treatment volume and maintenance of that positioning throughout the therapeutic life of the seeds. The importance of positioning has led to such techniques as computer aided treatment planning routines based on ultrasound or computed tomographic images (Feygelman, V. et al, "A Spreadsheet Technique for Dosimetry of Transperineal Prostate Implants", Medical Physics, 22, 97–100, 1995), ultrasound guided transperineal implantation for prostate cancer (Brosman, S. A. and Tokita, K., "Transrectal Ultrasound-Guided Interstitial Radiation Therapy for Localized Prostate Cancer", Urology, 38, 372–376, 1991) and conformal brachytherapy for carcinoma of the prostate (Osian, A. D. and Nori, D., "Conformal Brachytherapy for Carcinoma of the Prostate", Endocurietherapy/Hyperthermia Oncology, 10, 15–24, 1994).

Imaging technology is available which is capable of accurately locating the desired position for a seed, but holding the seed in the desired position has proven more difficult. U.S. Pat. Nos. 5,342,283, 5,030,195, 4,815,449, 4,754,745 and 4,697,575 all disclose devices intended to assist in initial placement and/or in maintaining placement of the seeds. The objective of all of the disclosed inventions is to provide a means to position discrete encapsulated sources. Positioning is of sufficient significance that a product based on U.S. Pat. No. 4,815,449 is commercially available. The expansion of brachytherapy to the treatment of additional disease types will be facilitated by, and in some cases will depend on, further improving positioning techniques.

The most common brachytherapy sources used for permanent interstitial implantation are small capsules, containing either iodine-125 or palladium-103, which are approximately 4.5 mm long and 0.8 mm in diameter. In some applications, such as prostate cancer therapy, the availability of a longer seed would be of value in maintaining positioning. However, due to the motion of the soft tissue surrounding the seed, vis-à-vis the rigid capsule of the seed, to use a longer seed would pose too great a likelihood of puncturing a surrounding organ or vessel.

A technique that improves the dose distribution without requiring a longer linear seed is the rigid seed string which is based on U.S. Pat. No. 4,815,449. This device consists of a linear array of iodine-125 seeds spaced at 1 cm center to center inside an absorbable suture material which has been stiffened by a proprietary process. One major drawback to using this device is that it has a tendency to become lodged in the implanting needle due to the effects of moisture on the suture material. Furthermore, this device does not include the ideal source, i.e., a continuous linear source, but rather relies on a series of separated, discrete sources in a line.

Clinical studies indicate brachytherapy sources could provide beneficial therapy in some tumor types where implantation of the seeds directly into the tissue is not possible, for example in the treatment of lung cancer (Nouri, D., "Intraoperative Brachytherapy in Non-Small Cell Lung Cancer", Seminars in Surgical Oncology, 9, 99–107, 1993) In such cases it is useful to insert a series of seeds inside suture material so that they can be sewn into or over the diseased tissue. A commercial product is available from Amersham Healthcare, Model 6720 I-125 Seeds in Carrier, consisting of iodine-125 seeds, spaced at 1 cm center to center, inside suture material. While this product offers a means of attachment, it suffers from representing a series of separated discrete sources rather than a more desirable continuous line source.

Furthermore, a major drawback for metal-encapsulated seeds is that the encapsulating metal absorbs a significant fraction of the radiation emitted by the contained radioisotope, for example about 14% of the iodine-125 X-rays and 40% of the palladium-103 X-rays are absorbed in the encapsulating metal in the current commercial seeds. As a consequence, to obtain the desired radiation dose rate on the exterior of the seed, additional expensive isotope activity must be added to overcome the losses in the encapsulating metal. Also because it is necessary to seal the ends of the capsules, the effective thickness of the metal is not the same in all directions resulting in a radiation field around the seed which is not uniform, a fact that complicates treatment planning and raises the possibility of the existence of areas within the treatment volume in which the radiation dose is below that required to kill all tumor cells present.

Thus the current practice of brachytherapy based on the use of discrete encapsulated sources is limited by: 1) the need to associate groups of discrete seeds together by some means so that they can be placed into tissue in a predetermined array and held in that array throughout the therapeutic life of the sources, 2) the need for complex treatment planning that takes into account the discrete nature of the seeds and the shape of the radiation field around each seed with the assumption the field shape around each seed is the same, 3) the need to add excess expensive isotope to compensate for the radiation absorption in the encapsulating metal, and 4) the creation of a nonuniform radiation field around the source because the effective thickness of the encapsulating metal is not the same in all directions. The present invention as disclosed herein, significantly reduces each of these limitations and furthermore allows a more complete realization of the potential benefits of brachytherapy.

DEFINITIONS

The description of the present invention is facilitated by the use of the following terms which are used in this patent specification and the claims as defined herein:

The term "polymeric" means composed of organic polymers, including silicones, whether naturally occurring or synthetic, and whether homopolymers or copolymers.

A "radioactive composite" is a substance that consists essentially of a radioactive powder and a polymeric matrix. In accordance with the present invention, the particles of radioactive powder are dispersed within the polymeric matrix essentially randomly throughout a particular volume thereof.

"Therapeutic sources" that can be fabricated from the radioactive composite include a structure that is solid in cross section, e.g. a right circular cylindrical rod; a structure that is hollow in cross section, e.g. a right circular cylindrical hollow tube; a suture (such as a monofilament or a multifilament thread, cord or string); a mesh; a film; a sheet; and microscopic, essentially monodisperse spheroidal sources.

An "applicator" is a device used to conform a therapeutic source to the shape of a body cavity so as to hold it in place during the period of treatment. Examples of applicators include the Fletcher-Suit and Manchester applicators.

The "average dimension" of one of the very fine radioactive particles of the radioactive powder is the average of the maximum and the minimum dimensions of the generally irregularly shaped particles.

SUMMARY OF THE INVENTION

The present invention provides a novel means for using a therapeutic source without requiring a metallic capsule, thereby producing a radiation field that is substantially uniform in all directions. This novel means is provided by a novel substance, defined as a "radioactive composite," that comprises very fine particles of radioactive material and a polymer. The therapeutic source is assembled from this radioactive composite so as to emit the desired amount of therapeutic radiation when it is used in a patient. In the context of this disclosure, the term "patient" includes any living organism requiring treatment, whether or not human.

The present invention provides a radioactive composite made by mixing very fine radioactive particles, i.e a radioactive powder, with a polymer, at the time of manufacture, wherein the radioactive material is randomly and essentially uniformly distributed within at least a defined portion of the polymer. This uniformity is a consequence of the large number of particles per unit volume of the polymer and the small size of these particles.

Radioisotopes applicable for use in the present invention include but are not limited to palladium-103, yttrium-90, gold-198 and phosphorus-32.

In preferred embodiments of the present invention, the polymeric matrix is a biocompatible polymeric matrix. Suitable biocompatible materials used for making the biocompatible polymeric matrix include the materials listed in Table 1 and Table 2.

Heretofore, brachytherapy sources intended for permanent interstitial implantation have included a metallic capsule to contain the radioactive material. A significant drawback of these metallic capsules is their non-uniform absorption of the emitted radiation, which causes a reduced radiation dose in certain directions. By eliminating the need for metallic capsules, the present invention overcomes the limitations inherent in their use, thereby allowing the full benefits of therapeutic irradiation from an implanted brachytherapy source.

Brachytherapy devices intended for temporary implantation using iridium-192 also have been designed to work in the absence of a metallic capsule. However, these unencapsulated iridium-192 sources are hazardous to the patient as well as the medical personnel involved, due to the high energy of the radioactive emissions. In addition, these implanted radioactive sources can only be left in place temporarily, causing the patient to undergo both an implantation and a removal procedure, resulting in medical personnel being exposed twice to the radiation hazard.

Conventionally, interstitial implantation of therapeutic radioactive sources is accomplished by placing discrete radioactive sources in a regular three dimensional array in the living body. To a first approximation each radioactive source may be thought of as a separate point source. One drawback of this conventional configuration is that the three dimensional radiation field generated is non-uniformly distributed in all directions and therefore requires considerable effort to be expended by way of imaging, special placement tools and internal spacers in order to assure that the discrete sources are precisely spaced. In contrast, the present invention substitutes a line source for this linear array of discrete radioactive sources, which results in a radiation field which is uniform along its length, and thereby generates a therapeutic array in which any non-uniformity is confined to two dimensions, because the third dimension is forced to be uniform. Thus the substitution of a radioactive line source for a series of discrete radioactive sources in a regular three-dimensional array, simplifies treatment planning, and source placement, and thereby reduces the potential for an area within the treatment volume from receiving a radiation dose that is inadequate to achieve the desired therapeutic effect.

The present invention includes radioactive composites, methods of making radioactive composites, methods of using radioactive composites, materials that are part of radioactive composites, as well as therapeutic sources that are made of or contain radioactive composites.

The therapeutic sources of the present invention can be designed and used as a temporary implant such as one intended to be physically removed after a defined time period or one intended to disintegrate (e.g. to be degraded and/or absorbed by the living body) over a defined time period. Alternatively therapeutic sources of the present invention can be designed to be a permanent implant, i.e., intended to remain for the patient's lifetime.

The very fine radioactive particles of the present invention are microscopic and are generally irregularly shaped. The "average dimension" (defined as the average of the maximum and the minimum dimensions) for a suitable radioactive particle can be from 0.002 microns to 20 microns. In preferred embodiments the range is from 0.005 microns to 10 microns. In the most preferred embodiments of the present invention, the range of dimensions is from 0.1 micron to 2 microns. These sizes are in direct contrast to conventional brachytherapy seeds, which are macroscopic in size, e.g. a conventional iodine-125 seed and palladium-103 seed is 4.5 mm long by 0.8 mm in diameter.

The very fine radioactive particles are different from conventional radioactive seeds in important properties other than size. For example, the preparation of the radioactive particles differ from the manufacture of conventional seeds in that the seeds are assembled individually from various components via an expensive manufacturing process, whereas a radioactive powder used in the composite of the present invention can be prepared inexpensively in bulk via a chemical reaction, for example, reduction of metal salts in microemulsion systems. As a result of this difference, production of the radioactive composite of the present invention can be far less costly and far less time consuming than the fabrication of conventional seeds.

In addition, the present invention provides a unique manner for incorporating radioactive material into a therapeutic source. For example, U.S. Pat. No. 5,030,195 teaches that first a mesh or film of polymeric material is formed, and then afterwards radioactive seeds are placed onto it, one at a time. In contrast, the desired film of the present invention may simply be formed in a single step, such as by extrusion or molding from the radioactive composite containing the radioactive particles, and likewise a mesh may be woven or otherwise formed directly from a suture of the present invention.

The present invention provides for varying the amount of radioactivity used for any particular therapeutic purpose. In some embodiments the amount of radioactive particles dispersed in polymer may be chosen from within an acceptable range when the radioactive composite is fabricated. In other embodiments, the amount of radioactivity per particle is selectable at the time of fabrication by either adjusting the amount of the radioisotope added per unit mass of the material making up the remainder of the radioactive particle's mass, by varying the size of the radioactive particles or both. In a third type of embodiment, the dose is adjusted by varying both the radioactivity per particle and the number of particles dispersed in the polymer as described above.

Still other embodiments allow the therapeutic dose to be varied on the basis of the length of time the therapeutic device is in contact with the tumorous tissue. An embodiment of this type is fabricated to provide the desired dose of therapeutic radiation during a brief period, such as from a few minutes to a day. The therapeutic source of this embodiment serves as a brachytherapy source while it is temporarily associated with the patient, during the prescribed time period. In a preferred embodiment the therapeutic source is temporarily inserted into the patient by means of a catheter.

In one aspect of this invention, the therapeutic source is used to treat a specific localized area in the body of the patient. The therapeutic source is fabricated so that it retains the radioactive particles for at least a defined period of time. In one embodiment of this aspect of the invention the therapeutic source is constructed such that the polymer retains the radioactive particles permanently, preventing any contact between the radioactive material and the patient's body fluids and tissues. In such embodiments, the polymer is permanent and not adapted to be degraded and/or absorbed by the body.

In another embodiment of this aspect of the invention, the polymer material is adapted to be degraded and/or absorbed by the body. In preferred embodiments thereof, the polymer is selected to disintegrate in the body at a predetermined rate, the rate chosen depending upon the half-life of the radioisotope used in the therapeutic source.

In one use of such an embodiment, the polymer in the therapeutic source is eliminated by the body over time, leaving behind only a small amount of residue from the radioactive particles. In a preferred use, the dissolution time is chosen to be sufficiently greater than the radioactive half-life of the radioactive material, insuring that the remaining radioactivity due to the residue no longer poses a hazard as it migrates from the treatment volume. In a more preferred use of this embodiment, the dissolution time is chosen to be between 10 and 15 times the half-life of the contained radioisotope so that the amount of radioactivity remaining in the residue is between 0.1% and 0.003% of the initial activity.

In a preferred use of such an embodiment, the radioactive particles are comprised of a material which is biocompatible, i.e., chemically inert in bodily fluids and evokes no toxic response when released into the body, so long as the amount of radioactivity remaining in the residue is no more than 0.1% of that originally present. Suitable biocompatible radioactive materials include pure metals, such as palladium particles or gold particles, or coated metals such as palladium particles coated with a layer of a biocompatible material such as titanium, platinum, gold, or a graphite deposit, and insoluble oxides of metals such as yttrium oxide ceramic particles.

Alternative biocompatible radioactive particles include those comprising radioactive materials which are not themselves biocompatible but become so when they are part of an alloy. These alternative embodiments also may be used to provide a powder which can be incorporated into the radioactive composite.

In one aspect of the invention the therapeutic source is used in the treatment of diseased tissue according to the normal practice of brachytherapy in which brachytherapy sources are implanted. A type of diseased tissue which may desirably be treated by this invention is neoplastic tissue. Examples of diseases involving neoplastic tissue include prostate cancer, lung cancer, cancer of the pancreas, breast cancer, head and neck tumors, melanomas or generally solid tumors in soft tissue.

Forms of the therapeutic source comprising the radioactive composite include a structure that is solid in cross section, e.g. a right circular cylindrical rod; a structure that is hollow in cross section, e.g. a right circular cylindrical hollow tube; a suture (such as a monofilament or a multifilament thread, cord or string); a mesh; a film; a sheet and microscopic, essentially monodisperse spheroidal sources.

In one preferred embodiment the therapeutic source is a cylindrical rod, solid in cross section, manufactured to have a preselected degree of flexibility. In a second preferred embodiment the therapeutic source is a cylindrical rod, hollow in cross section. The cross section may be circular, or it may be elliptical or another shape as appropriate. The ends of such rods may be cut at right angles to the axis of the cylinder, or they may be oblique or specially shaped.

A desired degree of flexibility is achieved by choosing the appropriate polymer grade from the commercial supplier of the polymer to comprise the radioactive composite. For suture material, a greater degree of flexibility is desired, In yet another embodiment, microscopic, essentially monodisperse spheroidal sources can be fabricated from the radioactive composite. Such microscopic, essentially monodisperse spheroidal sources can then be used, for example, in the treatment of primary or metastatic cancer in the liver by infusing the microscopic, essentially monodisperse spheroidal sources into the hepatic artery, the blood flow therein carrying the microscopic, essentially monodisperse spheroidal sources into the capillary network of the liver where they are trapped and deliver their therapeutic dose of radiation. Such spheroidal sources may desirably have any particular diameter from 10 microns to 100 microns, and preferably about 20 microns. To disperse within the small size of the spheroidal sources, the radioactive powder used in this embodiment desirably has an average dimension of 0.002 micron to 0.1 micron.

In certain embodiments of the invention, the therapeutic source is placed in a delivery system and used to irradiate arterial walls and surrounding tissue to prevent restenosis, following procedures to improve blood flow through the artery. In a preferred embodiment the delivery system is a catheter and the therapeutic source is placed at the tip of the catheter. These embodiments can be used with any form of the therapeutic source that can be effectively delivered by these methods. In a preferred embodiment the therapeutic source is a monofilament attached to the distal end of the catheter. In another preferred embodiment the therapeutic source is a hollow tube slid over the tip of the catheter guidewire.

In other embodiments of this aspect of the invention, the therapeutic source is sewn into a diseased tissue in such a way as to deliver a palliative and/or a curative radiation dose to the diseased tissue. In a preferred embodiment the therapeutic source is in the form of a suture, which may be a monofilament or a multifilament thread, cord or string. Examples of applications for this embodiment include intraoperative brachytherapy in non-small-cell lung cancer and control of scar tissue in surgical closure lines.

In still another embodiment, the therapeutic source is a mesh woven or formed by bonding from a continuous suture fabricated from the radioactive composite, and the mesh is positioned in the cavity remaining after the surgical removal of the diseased tissue in such a way as to irradiate and subsequently kill any abnormal tissue remaining in or adjacent to the surgical margins. In a preferred embodiment the mesh can be woven at the time of surgery from radioactive suture, thereby allowing the health care provider to respond in the most appropriate way to the state of the disease as revealed during the surgical procedure.

In another embodiment, a therapeutic source in the form of a mesh, sheet or film is placed inside a cavity of the body to treat diseased tissue surrounding the cavity. The mesh, sheet or film may be used in association with an applicator, as for example an ophthalmic plaque to treat intraocular malignant melanoma.

One aspect of the present invention includes the various means that the radioactive composite can be "packaged." In some embodiments the radioactive composite is used alone. In other embodiments, the radioactive composite is contained within a second layer of polymeric material. In preferred embodiments of this type, the second layer of polymeric material is not radioactive. In yet other embodiments, the radioactive composite is encapsulated within a conventional metal seed. In still other embodiments the radioactive composite is wrapped around a non-radioactive polymeric core. In yet another form of this aspect of the invention, the radioactive composite is shaped in such a manner so that it encircles a hollow core. In the most preferred embodiments of this aspect of the invention, the radioactive composite contains a radiographically detectable element, e.g. a wire that is radiopaque to X-rays. It is emphasized that all of the embodiments of this aspect of the invention can be applied to all of the forms and shapes of the radioactive composite described herein.

Methods for fabricating therapeutic sources include extrusion, molding, and weaving.

In one aspect of the invention the therapeutic source is a rod that is made of a polymeric matrix manufactured to have a preselected degree of flexibility. The rod is adapted to be inserted into a tissue or an organ to provide a defined radiation field. In this aspect of the invention, the diameter of the rod can be 0.1 mm to 2 mm, with the preferred diameter being 0.2 to 1 mm, and the most preferred diameter being 0.4 to 0.8 mm. The rod can then be cut into any length, with the preferred length depending on the application and the individual circumstances. In preferred embodiments, the therapeutic source is adapted to be cut into short lengths for implantation as a conventional seed, with these lengths being any convenient length, for example from 4.5 mm to 6.0 cm.

In an application of this aspect of the invention involving prostate cancer, the 1-125 and Pd-103 sources have a length of 4.5 mm and are generally spaced 1 cm apart, center to center, when implanted. For prostate cancer, the preferred length ranges from 4.5 mm to 6 cm, a length allowing an entire linear array of discrete seeds to be replaced by a single length of this therapeutic source. Another preferred embodiment has a diameter of 0.8 mm, and is cut into lengths of 4.5 mm.

In another aspect of the invention, a therapeutic source in the form of a rod having preselected flexibility is made by applying a thin coating of a non-radioactive polymer over the radioactive composite. Biocompatible polymers, including those listed in Table 1 and Table 2, can be used as suitable materials to serve as this thin coating.

In another embodiment, a radiographically detectable, e.g. X-ray-opaque, marker wire is included in the rod along or near the long axis of the rod. Following implantation of this particular embodiment, the X-ray-opaque marker can be used to locate implants made from the radioactive composite, by external X-ray imaging. Alternative uses for embodiments containing an X-ray-opaque wire marker include but are not limited to visualization of the therapeutic source on a CT scan and the use of the wire to attach the source to a catheter. Materials that the radiographically detectable element can be made from include, but are not limited to, gold wire, platinum wire, and polymeric material containing a sufficient amount of radiopaque material, e.g. barium sulfate, so as to allow location of the therapeutic source and detection of its orientation by conventional X-ray imaging.

When the radioactive composite is formed in a continuous suture, either monofilament or multifilament, a preferred diameter is between 0.1 and 2.0 mm. This size range closely spans that of suture materials currently available in the medical market. One method for selecting the appropriate length of the radioactive suture to use, is to first determine the desired therapeutic radiation dose that is to be delivered by the suture when it is sewn into the diseased tissue, and then to choose the suture length necessary to deliver this dose on the basis of the radioactivity per unit length of the suture. In a preferred method, both the radioactivity per length of the suture, and the length of the suture are taken into account and jointly adjusted, in order to optimize the delivery of the desired therapeutic radiation dose.

One problem of the conventional brachytherapy sources currently in use is that they produce a reduced radiation dose in certain directions, and thereby create a non-uniform radiation field. Non-uniformity can create regions within the treated tissue where the radiation dose is insufficient to kill all of the diseased cells in that region. The present invention significantly reduces this problem by including embodiments for the therapeutic source, such as a right circular cylinder, manufactured to have a preselected degree of flexibility, that produces a radiation field which is more uniform. For example, the radiation field may be essentially cylindrical along isodose lines in close proximity to the source, having greater symmetry than that of any seed currently available.

In the application of brachytherapy to solid tumors, such as those found in certain diseased prostate glands, radiation therapists have recognized the value of maintaining the individual seeds in a predetermined array. The maintenance of the predetermined array is accomplished in the prior art by taking individual seeds and placing them into an absorbable suture material. The absorbable suture material is then stiffened to provide a group of seeds that are held in a linear pattern at a fixed separation distance. A number of these linear groupings of seeds are then inserted at predetermined spacings and angles into the prostate gland using hollow needles, thereby forming the desired three dimensional array of radiation source within the prostate gland.

By constructing the therapeutic source of the present invention in the shape of a right circular cylindrical rod embodiment, manufactured to have a preselected degree of flexibility, a treating physician is enabled to simply cut sections of the rod to the lengths desired for each of the linear groupings described above and then simply insert these pieces of rod into the diseased tissue. This procedure simply and inexpensively, allows the physician to fabricate any desired three dimensional array of the therapeutic source. Furthermore, the radiation field within the tissue of the present invention will be substantially more uniform because it is created by a series of continuous and uniform line sources.

When neoplastic tissue, such as a breast carcinoma, is removed surgically, the most likely site of recurrence is known to be in the region immediately surrounding the excised tumor. For this reason the surgical removal of such tumors is usually followed by extensive radiation therapy in this region. By constructing the radioactive composite of the present invention into forms such as radioactive sutures or a woven radioactive mesh, a simpler and safer method for irradiating such surgical margins with sterilizing doses of radiation can be accomplished; while still avoiding the damage that otherwise occurs to the surrounding tissue.

Restenosis is the process whereby an artery which has been opened by a technique such as balloon angioplasty, experiences a subsequent reduction in its open cross section, due to cell proliferation or plaque formation. Benign and relatively inexpensive techniques, such as balloon angioplasty, fail in approximately 40% of cases due to restenosis, thereby forcing physicians to perform more expensive, and more dangerous, procedures such as coronary artery heart bypass surgery. The present invention provides a radiation source capable of delivering a dose of radiation to an arterial wall which is intended to reduce the likelihood of restenosis, thereby reducing the number of patients who will ultimately require the more expensive and more dangerous procedures. The therapeutic source for this application is preferably a solid rod, manufactured to have a preselected degree of flexibility, or a hollow tube. Such a source must be flexible enough when associated with a catheter to be maneuverable into the treatment site.

The detailed description of the invention, provided below, will aid in the overall understanding of the invention. However, one skilled in the art will immediately realize that the methods, results and examples presented only help illustrate how the invention works and are not meant to limit the scope of the invention as defined by the appended claims.

BRIEF DESCRIPTION OF THE DRAWINGS

FIG. 3 is a blow-up of a small section of the rod of FIG. 1 showing radioactive particles essentially uniformly distributed within the radioactive composite.

FIG. 4 is a blow-up of a small section of an alternative embodiment to that of the rod of FIG. 1, in the same view as FIG. 3, showing radioactive particles that are essentially uniformly distributed within the radioactive composite, which are encapsulated by a biocompatible outer layer.

FIG. 7 is a partial cut-away perspective view of a solid right circular cylindrical rod made from a radioactive composite, which has a non-radioactive plastic outer coating including a sleeve, in accordance with the invention.

FIG. 8 is a partial cut-away perspective view of a hollow right circular cylindrical rod, made from a radioactive composite which has a hollow core, in accordance with the invention.

DETAILED DESCRIPTION

Figure 1:
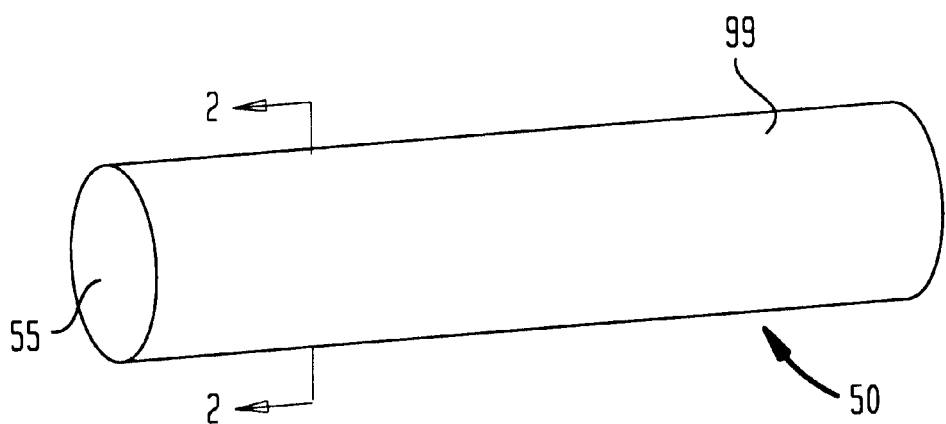
FIG. 1 shows a solid right circular cylindrical rod, made from a radioactive composite in accordance the invention.

Several considerations influence the choice of the size of the particles making up the radioactive powder mixed with polymer to compound the radioactive composite. These are discussed in two separate categories: mechanical considerations and radiation considerations.

Mechanical Considerations

Strength: The mechanical integrity of a polymeric therapeutic source such as a suture, mesh, film or sheet is influenced by the ratio of the volume of the radioactive particles to the volume of the polymer in the radioactive composite from which it is made.

The Mechanical Integrity Ratio or M.I. Ratio is defined as:

M.I. RATIO=VOLUME OF THE RADIOACTIVE PARTICLES/ VOLUME OF THE POLYMER

Experience indicates that as long as the M.I. ratio has an upper limit of 0.4 and provided that the largest radioactive particle dimension is small compared to the smallest dimension of the therapeutic source, the mechanical properties of the polymer will not be seriously diminished. A preferred upper limit for the M.I. ratio is 0.15.

The volume of radioactive powder required to provide therapeutic levels of radiation varies enormously, depending on the radioisotope chosen, how the isotope is prepared and the particular therapeutic application. For example, nuclear reactor produced Pd-103 can be generated in a palladium metal powder with a specific activity of around 30 Curies per gram. Thus, about 100 micrograms of radioactive particles prepared from this metal per centimeter of a monofilament, 0.8 mm in diameter, would correspond to a loading of 3 millicuries per centimeter. This is an appropriate activity for permanent interstitial implants for several cancer types. The volume of radioactive particles in this example corresponds to about 0.2% of the polymer volume, i.e, an M.I. Ratio of 0.002, which means that mechanical integrity of the polymer will not be impaired.

On the other hand, intralumenal applications for therapy have been proposed which would require temporarily inserting a source for a maximum period of only a few minutes to deliver the desired dose. To achieve the therapeutic dose in this short time requires a volume of palladium-103 containing particles around a thousand times greater, that is, essentially a metal particle volume that would correspond to a solid metal source. Thus it is not physically possible to prepare a useful radioactive composite for such a source using reactor produced palladium-103. However, cyclotron produced palladium-103 can result in radioactive palladium metal particles with a specific activity about 1000 times greater than that of reactor produced particles. Therefore, the preparation of a high dose rate therapeutic source does not pose a problem of mechanical strength provided cyclotron produced palladium-103 is utilized.

Handling and Mixing: The radioactive particles and polymer must be brought together in some way to begin the formation of the radioactive composite. Normally, commercial polymers are supplied in cylindrical pellets approximately 3 mm in diameter and 3 mm long. If such pellets and the radioactive particles are handled dry, the size of the radioactive particles becomes important because particles smaller than 1 micron tend to become airborne and remain suspended, creating problems in mixing and radiation control.

Radiation Considerations

Therapeutic Source Uniformity: The radioactive particles should be uniformly mixed in the polymer in order to produce a radiation field that does not vary significantly from source to source. The 0.8 mm diameter monofilament, from the example above, is useful to illustrate this feature. When the radioactive particles have a 20-micron diameter, for example, there are approximately 2,000 particles per centimeter of monofilament. The standard deviation from a uniform distribution of particles, for a given length of monofilament, is the reciprocal of the square root of the number of particles in that length of monofilament, assuming the particles are all substantially the same size. Choosing the length of the monofilament to be 0.45 cm, which is the approximate length of a currently available commercial palladium-103 seed, the standard deviation from a uniform distribution of particles in this particular example is ±3%.

If a manufacturing tolerance of 7.5%, for example, were to be considered an allowable variation between maximum and minimum activities of two seeds in an implanted therapeutic array, then only 75% of the seeds described above would meet that criterion. From this calculation it is concluded that 2000 particles per cm are too few to produce therapeutic sources with a degree of uniformity at the aforementioned level. Accordingly, for this example, either the particles of the powder should be smaller, or the radioactive palladium from which the powder is made should be diluted with more nonradioactive palladium, so as to increase the number of particles per centimeter of the monofilament, while keeping the source strength the same.

The mass of a particle varies with the cube of diameter, so that if 2-micron particles were used in the above example, there would be 1000 times more particles per centimeter. The standard deviation for a 0.45 cm monofilament would then be ±0.1 percent. This illustrates the strong dependence of uniformity on number of particles in a source.

Self Shielding and Efficient Use of the Radioisotope: Depending upon the radioactive isotope, i.e. the energy spectrum of the emitted radiation, the size of the particle can affect the amount of radiation observed outside the particle. The practical consequence of this is that as particles get larger, more isotope must be added per unit mass of material making up the particle to generate a comparable radiation field around the particle, i.e., in terms of isotope utilization, source production becomes less efficient and more costly as larger particle sizes are used in the radioactive particulate. In the case where the radioactive isotope is the same element as the material making up the remainder of the radioactive particle, this effect is called self shield. For example, in the above monofilament case palladium X-rays are strongly self shielded by palladium metal. The 20 micron diameter particle, assuming it is roughly spherical, would absorb around 20% of the palladium X-rays emitted by the particle. By comparison, a particle of one micron radius would absorb only around 2% of its own radiation. The consequences of self shielding are primarily economic. That is, the more self shielding, the more radioactive isotope is required to produce a therapeutic source. Accordingly, 20 micron particles are also the upper limit for particle size in the present invention.

Anisotropy: Bulk self shielding refers to the absorption of radiation by the radioactive composite rather than within the metal particle itself. For example, in the above monofilament example, if individual seeds are made by cutting the monofilament into 0.45-cm lengths, the bulk shielding produces a non-isotropic radiation pattern around the seed. The radiation field is approximately 20% less intense directly along the axis of the seed than perpendicular to the seed. The anisotropy of the present invention is, however, substantially less than the values of the 60% to 80% observed in commercially available iodine-125 and palladium-103 seeds.

Effects on the Polymeric Matrix: The mixing of a radiation source directly in a polymer results in a large radiation dose being delivered to the polymer over time. In the palladium monofilament example, the total dose delivered to the polymer is around 400,000 centigray. While this level of radiation is well within the tolerance levels of the polymers listed in Table 1, this consideration is important in the design of therapeutic sources from radioactive composites. For example, the palladium-103 intralumenal source referred to above would deliver a dose to the polymer of approximately 400,000,000 centigray. Such large radiation doses greatly reduce the number of suitable polymers. In this case, of the polymers listed in Table 1, only polyetherimide would be appropriate.

The Illustrated Structures

As shown in the accompanying figures, the present invention can be accomplished using a radioactive composite in any of various shapes, one being the form of a right cylindrical therapeutic source 50. The therapeutic source 50 may be formed by extrusion of a radioactive composite material through a circular die, or it can be molded or constructed from a radioactive composite by another appropriate means into an elongated right circular cylinder. This cylinder may have been manufactured to have a preselected degree of flexibility which is rigid, in which case it is referred to as a rod, or it may be flexible, in which case it is referred to as a monofilament or suture. In either form, it can be produced or cut into lengths appropriate for a particular brachytherapy application.

The ends 55 of the therapeutic source 50 may be planar, as shown, or may be tapered or shaped in another desired way.

Figure 2:
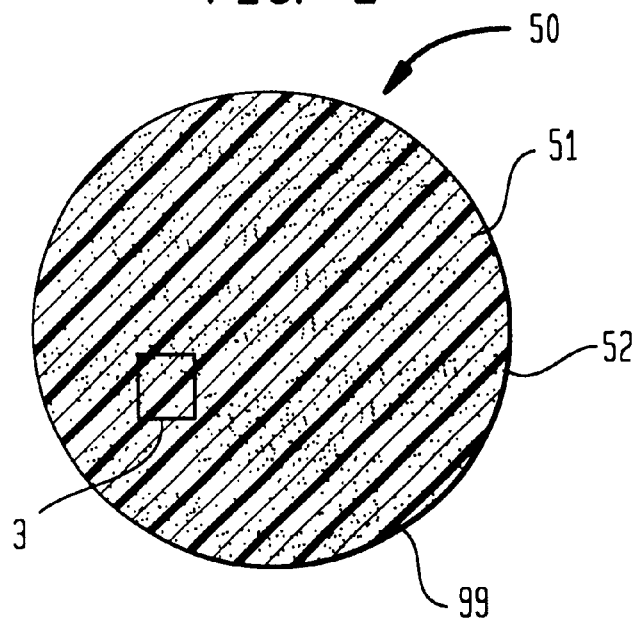
FIG. 2 is a sectional view of the embodiment of FIG. 2 taken through lines 2—2. In the sectional drawings herein, the alternating thick and thin diagonal lines provide conventional shading to represent polymeric material, and the small dots represent particulate matter randomly dispersed therethrough.

As shown in the cross-sectional view of FIG. 2, a polymeric matrix 51 contains dispersed throughout a multiplicity of very fine radioactive particles 52. Such a random dispersion of very fine radioactive particles throughout a polymeric matrix forms the radioactive composite 99 of the present invention. Throughout the drawings, the radioactive composite is identified by reference numeral 99. The drawing is shaded to represent the polymeric material of the matrix 51, manufactured to have a preselected degree of flexibility, and the dispersed particles 52 are diagrammatically represented by dots. (The lead line from reference numeral 52 terminates at a small dot. The position and number of the dots representing the particles 52 are not to be taken as literal illustrations of position, size or quantity.) Corresponding elements in other figures are represented by the same drawing convention.

The polymeric material can be in the form of biocompatible plastic, such as those listed in Table 1, which, when implanted into a living body, remain essentially unchanged, thereby permanently retaining the radioactive particles.

Other appropriate biocompatible plastics for the polymeric material are those which, when implanted into the living body, dissolve at well characterized rates, thus leaving behind the particles to be incorporated into the local tissue or to be redistributed or excreted from the body. Some examples of such materials are listed in Table 2, other examples include Victyl and PDS sold by Ethicon, Inc. Other suitable materials are offered for sale by American Cyanamid.

In general, a biocompatible material is one that passes appropriate biological tests for short-term or long-term toxicity as defined in the Tripartite Guidance or ISO 10933-1.

FIG. 3 is a blowup of a small section of FIG. 2, showing the irregularly shaped radioactive particles 52 dispersed in the matrix 51, forming together the radioactive composite 99 of the present invention.

FIG. 4 illustrates an alternative embodiment of the invention, in which radioactive particles 42 are coated with a layer 43 of biocompatible material such as titanium, platinum, gold, or a graphite deposit, or insoluble oxides of metals such as yttrium oxide ceramic particles, and then dispersed within a polymeric matrix 41 to form a radioactive composite 99 of the present invention. Such a radioactive composite 99 could alternatively be fabricated into any of the shapes that are illustrated, described and suggested herein.

The very fine radioactive particles are small in size, e.g. 20 angstroms to 50 microns, and contain the radioisotope in an appropriate medium. In its simplest form, the particles consist of the same element as the radioisotope used. For example in the case when the radioactive material is Pd-103, these particles might consist of natural palladium metal into which an appropriate amount of Pd-103 has been incorporated. See, e.g., aforementioned U.S. Pat. No. 5,405,309.

Any of a number of processes for preparing the radioactive powder is appropriate. For example, upon the addition of the reducing agents formic acid or hydrazine to a hot solution of palladium chloride, palladium metal precipitates in the form of small particles. These particles are often referred to as palladium black. The same effect can be obtained by bubbling the reducing gases hydrogen or ethylene through a palladium chloride solution. Smaller particles with a narrow size distribution can be produced by the methods of sol/gel technology, as for example by the method of Boutonnet (Boutonnet, M., Kizling, J. and Stenius, P., "The Preparation of Monodisperse Colloidal Particles from Microemulsions," Colloids and Surfaces, 5, 209–225, 1982).

Another way to form the very fine particles is by incorporating the radioisotope into a ceramic material. The isotope yttrium-90 (Y-90) can be created within a medium formed from $Y_2O_3$ or $Y_2O_3$ and other appropriate glass forming oxides. Yttrium oxide particles can be prepared, for example, by firing the oxide in a solar or other high temperature furnace to form the ceramic, grinding the ceramic into fine particles, and then sieving them to obtain the desired size range. This procedure greatly reduces the solubility of the oxide in body fluids.

Yet another radioactive material that can be used in the present invention as very fine radioactive particles is gold-198. Gold-197 may serve as a precursor isotope and then be transmuted by bombardment with neutrons, for example. This transmutation of a gold-197 target with neutrons, produces gold-198 together with some gold-199. For simplicity this transmutation is referred to hereinafter as the production of gold-198. Techniques for making suitable gold colloids for this aspect of the invention are well known in the art, e.g., Slot, J. W. and Geuze, H. J., Eur. J. Cell. Biol., 38, 87, 1985. Monodisperse gold colloids having average particle diameters of 5 nm, 10 nm and 20 nm, respectively, are available commercially from Sigma Chemical Company, St. Louis, Mo., U.S.A.

When the very fine particles are to be released into the body by disintegration of the matrix, e.g. from an absorbable polymeric matrix, the particles themselves must be biocompatible. The present invention includes biocompatible radioactive particles that are made in a large variety of ways. For example, one way is by preparing palladium particles that are not known to produce any toxic reaction when implanted interstitially. Thus Pd-103 particles can simply be prepared by combining Pd-103 chloride with the palladium chloride solution mentioned above and using any of the reduction reactions cited. Yttrium oxide particles derived from the ceramic have also been permanently implanted in the body without reported toxic effects.

An alternative method for constructing biocompatible radioactive particles is by coating the particles with a thin layer of a biocompatible material to improve their compatibility, should such be required. For Pd-103, examples of suitable coatings include those prepared from biocompatible plastic, titanium, gold, platinum or pyrolytic carbon. Examples of suitable coatings for yttrium oxide include those prepared from titanium or pyrolytic carbon.

Methods for coating the radioactive particles with metals include but are not limited to using a vacuum coating process such as resistive heating evaporation, sputtering, or electron beam evaporation. A preferred method for applying a plastic coating is by solvent evaporation in a fluidized bed. A preferred method for applying a pyrolytic carbon coating is by standard chemical vapor deposition methods.

The methods described above are meant only as specific examples of the present invention and any person skilled in the art would be enabled to make and use alternative embodiments employing analogous materials including but not limited to those that have been listed throughout this specification.

Figure 5:
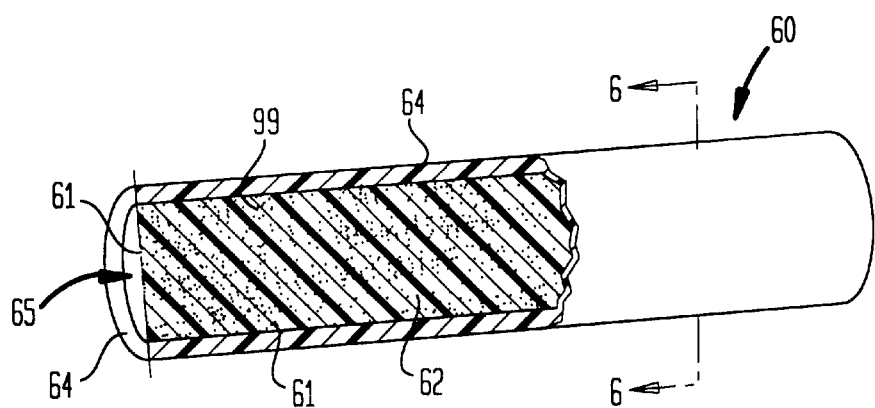
FIG. 5 is a partial cut-away perspective view of a solid right circular cylindrical rod, made from a radioactive composite which has a non-radioactive plastic outer coating, in accordance with the invention.
Figure 6:
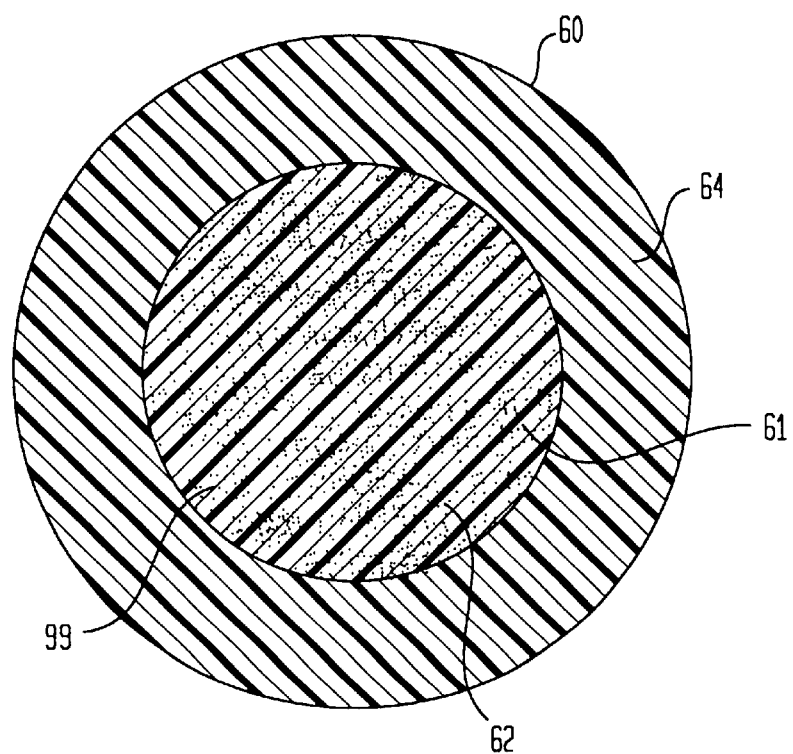
FIG. 6 is a sectional view of the embodiment of FIG. 5 taken through lines 6—6.

In FIGS. 5 and 6, an alternative embodiment of a right cylindrical therapeutic source 60 includes a right cylinder formed of polymeric matrix 61 containing finely dispersed radioactive particles 62. Surrounding the radioactive composite 99 is a sleeve 64 of polymeric material. The sleeve 64 may be fabricated from the same substance as that of the polymeric matrix 61 or from a different substance. The ends 65 of the therapeutic source 60 may be flat, as shown, or shaped differently. This embodiment can be fabricated by co-extrusion through a cross head die. One advantage of this embodiment is the absence of any radioactive material on any surface of the cylinder except the ends, thus reducing the potential for even low level releases of the isotope.

In certain instances sleeve 64 of the embodiment of FIGS. 5 and 6, or sleeve 74 and cap 75 of the embodiment of FIG. 7, are of sufficient thickness to either absorb a portion of the radiation emitted, or to modify the energy spectrum of the emitted radiation. By serving as a means for lowering the intensity and/or average energy of the beta particles emitted by the encased radioactive particles, the coaxial plastic coating of these embodiments can be used to adjust the emitted radiation of the radioactive particles encased within the therapeutic source and thereby aid in the adjustment of the dose rate in brachytherapy. The use of alternative thicknesses for the polymeric outer layer enables physicians and veterinarians to select the proper embodiment that will allow the desired dose to be administered. Preferred radioactive particles for the use of this embodiment in these instances contain radioisotopes such as yttrium-90 or phosphorus-32, i.e., reducing the average energy of beta particles emitted and creating bremstrahlung.

In FIG. 7, an alternative embodiment of a therapeutic source 70 of the present invention is shown, one that in addition has a polymeric sealing layer placed over the two ends. As in the embodiment of FIGS. 5 and 6, the therapeutic source 70 contains a polymeric matrix 71 throughout which is dispersed radioactive particles 72, the radioactive composite 99 being surrounded by a polymeric sleeve 74. However the sleeve 74 does not terminate at a planar end but rather is sealed by a cap 75 at each end of the source 70. The cap 75 may be made from the same polymeric material as the sleeve 74 or from a different polymer, and is sealed to the sleeve 74. This feature allows a therapeutic source to be completely isolated from its environment. This embodiment eliminates the possibility of the therapeutic radioisotope being leached out of the source into the body of the patient by having an outer-layer free of radioactive particles.

One method of forming an end-sealing layer is accomplished by dipping the ends of the therapeutic source in a polymer solution and then allowing the solvent to evaporate. Alternative methods include heat sealing a plastic film over the end, ultrasonic welding and by cement. Although illustrated in the context of the present embodiment, such a cap may advantageously be employed with any embodiment of the present invention where the outer layer does not incorporate radioactive particles.

Figure 9:
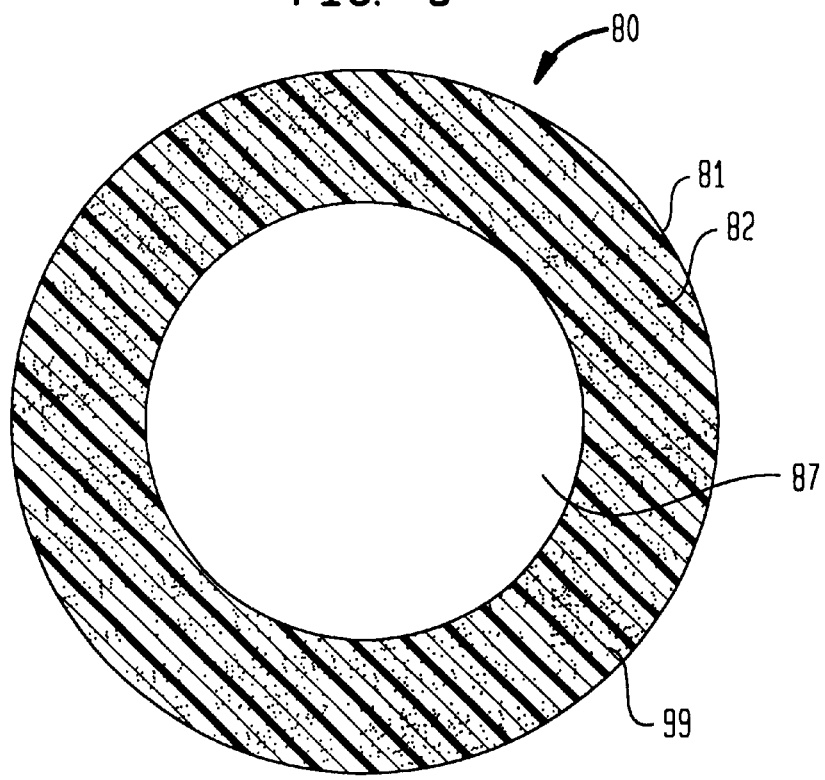
FIG. 9 is a sectional view of the embodiment of FIG. 8 taken through lines 9—9.

FIGS. 8 and 9 show an alternative embodiment of a therapeutic source 80 in the form of a hollow right cylinder. Polymeric matrix 81 incorporates radioactive particles 82. A lumen 87 passes through the cylindrical source 80. This lumen can be used in a variety of ways including to provide a simple mechanism for the attachment of the cylinder to a catheter tip for an application such as intraarterial irradiation. If short lengths, approximately 0.5 cm or less, of the therapeutic source are required, it is easily fabricated by molding over a pin. If longer lengths of the source are required, standard tubing extrusion techniques may be used. For intralumenal applications, the outer diameter of the tube could vary from 0.2 mm to 2 mm and the inner diameter from 0.1 to 1.5 mm. For interstitial applications the outer diameter can be between 0.2 mm and 2 mm with the inside diameter varying between 0.1 mm and 1.5 mm. For intracavitary applications the outer diameter could be between 0.2 mm and 5 cm with the inner diameter between 0.1 mm and 4.75 cm.

Figure 10:
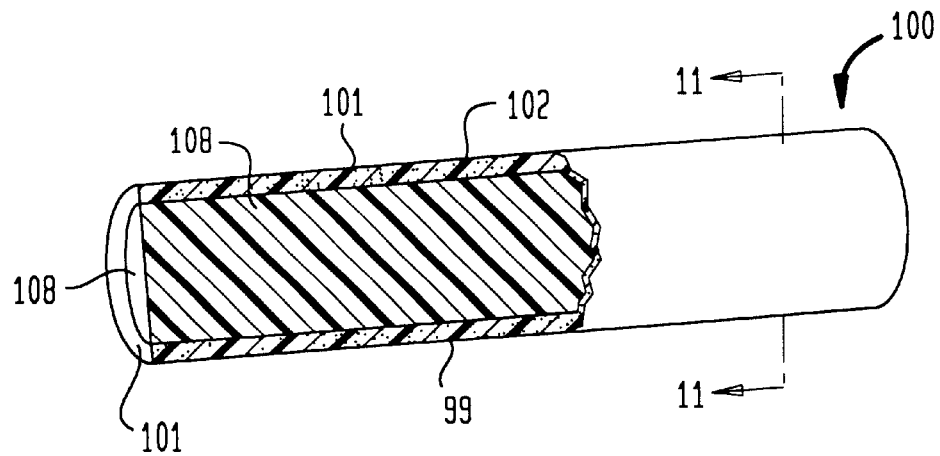
FIG. 10 is a partial cut-away perspective view of a solid right circular cylindrical rod, made from a radioactive composite which has a non-radioactive plastic inner core, in accordance with the invention.
Figure 11:
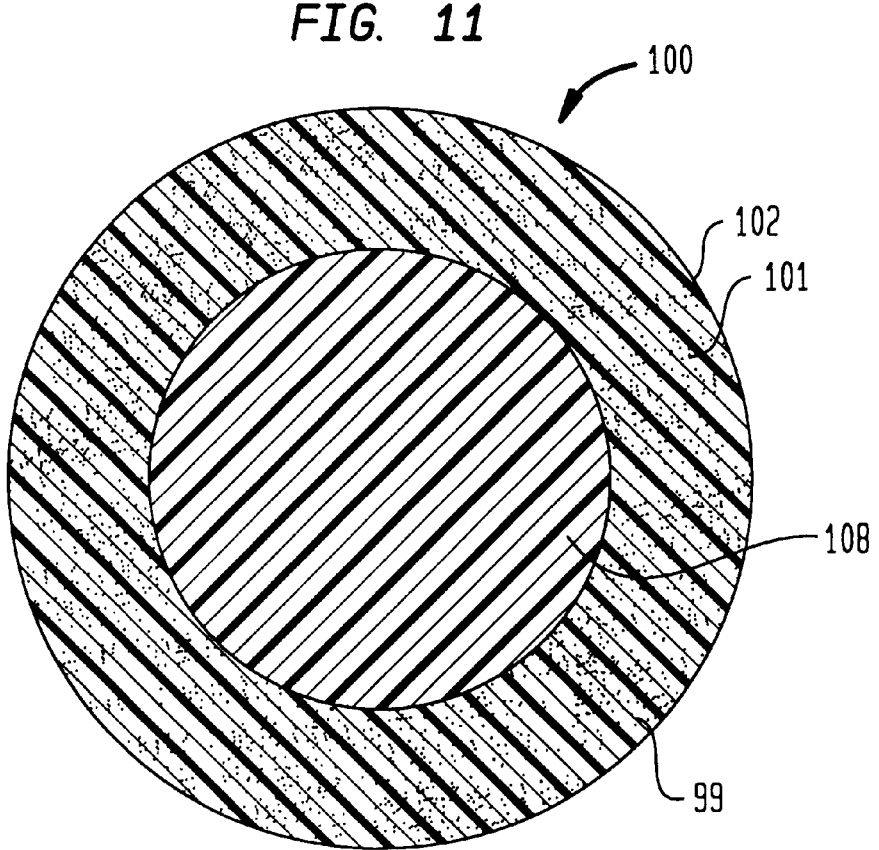
FIG. 11 is a sectional view of the embodiment of FIG. 8 taken through lines 11—11.

FIGS. 10 and 11 show an alternative embodiment of a therapeutic source 100 in the form of a hollow polymeric matrix 101 having radioactive particles 102 dispersed therethrough. A polymeric core 108 extends axially through the center of the source 100. This embodiment also can be fabricated by such techniques as co-extrusion using a cross head die. In this embodiment all the radioactive material is present in element 99, on the outer layer of the cylinder, thereby reducing the average distance between the radioactive particles and the tissue to be treated, as well as reducing the average distance a photon of emitted radiation must travel before escaping the therapeutic source. This embodiment can be used in applications where a very high radiation dose rate is required or the path through the plastic followed by the photons emitted by the contained radioisotope must be minimized. An application for this embodiment is as a therapeutic source in which a beta-emitting isotope, such as yttrium-90 or phosphorus-32, is the contained radioisotope.

Due to the absence of a surrounding polymer that would otherwise absorb some of the beta particle emission, designs such as this one may be used to facilitate applications which require high dose rates, like intraarterial brachytherapy.

Figure 12:
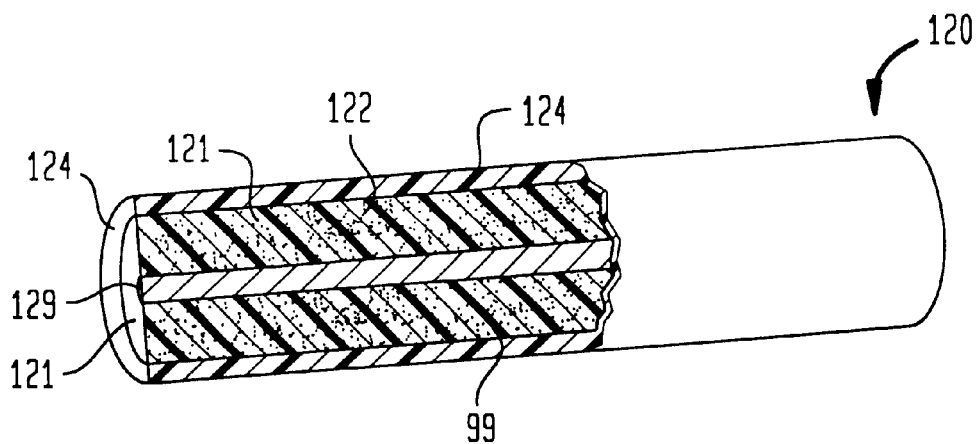
FIG. 12 is a partial cut-away perspective view showing an alternative embodiment to that of FIG. 5, wherein a metal wire is in the center of the source.

FIG. 12 shows an alternative embodiment of the therapeutic source 60 shown in FIGS. 5 and 6. The therapeutic source 120 shown in FIG. 12 has a polymeric matrix 121 through which radioactive particles 122 are dispersed and around which a polymeric sleeve 124 extends. However, extending through the axis of the radioactive composite 99 of the source 120 is a metal wire 129, which is a radioopaque material, for example gold or stainless steel, and which thereby facilitates locating the source 120 in a patient by X-ray photography or fluoroscopy.

As is also true for the embodiments described in FIGS. 13–15 below, the therapeutic source of FIG. 12 can be extruded by standard techniques, in the manner in which plastic insulation is routinely applied to electrical wiring, using a cross head die. These therapeutic sources, in their low activity embodiments, can be used in interstitial implants and to facilitate the location of the implant in the patient allowing a health care provider to verify that the location of the source(s) is in accordance With the treatment plan. Should the implant migrate to another area within the body, this embodiment can be used to assist the health care provider in precisely locating the source.

Figure 13:
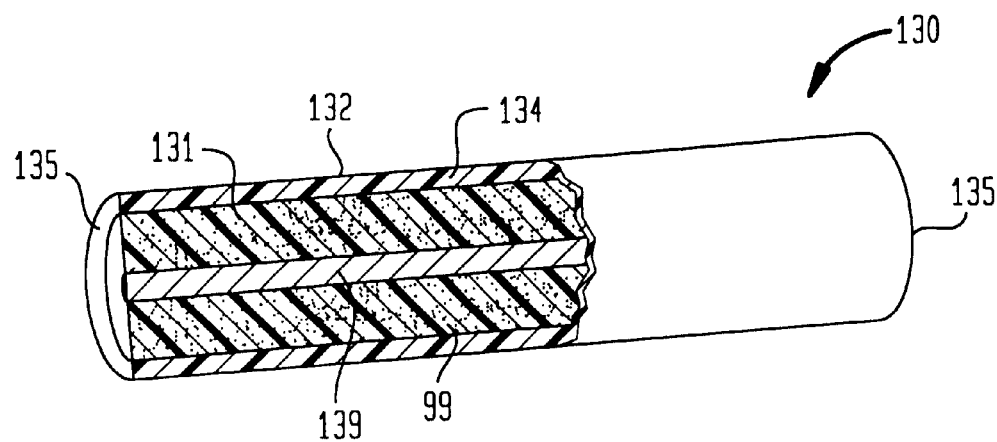
FIG. 13 is a partial cut-away perspective view showing an alternative embodiment to that of FIG. 7, wherein a metal wire is in the center of the source.

FIG. 13 shows an alternative embodiment of the therapeutic source 120 shown in FIG. 12. The therapeutic source 130 of FIG. 13 has a polymeric matrix 131 through which radioactive particles 132 are randomly dispersed in the form of a radioactive composite 99 of the present invention. Extending through the axis of the radioactive composite 99 of the source 130 is a metal wire 139, which is radioopaque, and which thereby facilitates locating the source 130 in a patient by X-ray photography or fluoroscopy. A cap 135 of polymeric material, which may or may not be the same material as that of sleeve 134, covers each end of the source 130.

Figure 14:
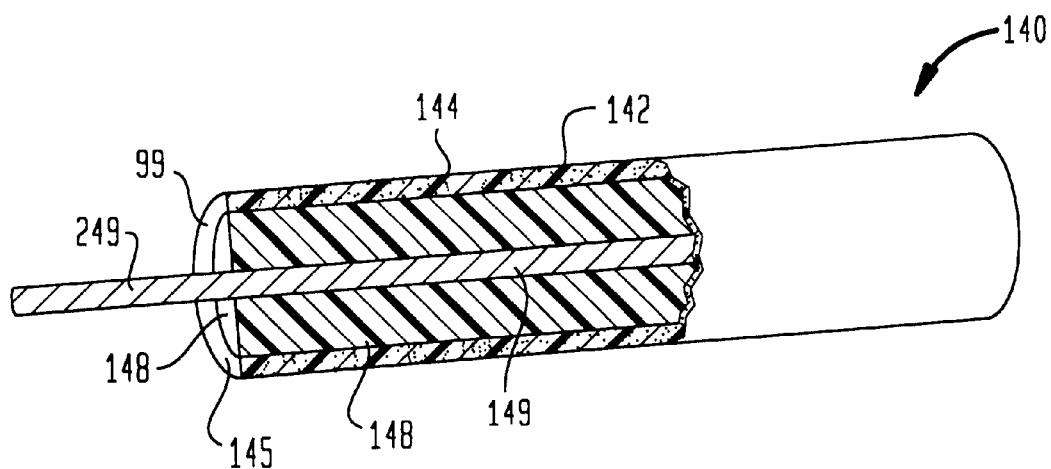
FIG. 14 is a partial cut-away perspective view showing an alternative embodiment to that of FIG. 10, wherein a metal wire in the center of the source includes a tail portion that extends beyond the end of the radioactive composite.

As shown in FIG. 14, a therapeutic source 140 is formed of a tube of radioactive composite 99 which is similar to that shown in FIGS. 10 and 11. Radioactive particles 142 are randomly dispersed in polymeric matrix material 141, and a nonradioactive core 148 of polymeric material extends therethrough similarly to that of element 108 of the embodiment of FIG. 10. A wire 149 extends axially through the core 148 in a manner similar to that of wire 129 in FIG. 12, except that the wire 149 includes a tail portion 249 extending beyond the end 145 of the radioactive composite 99 and nonradioactive core 148. In use, the tail may be spot welded to a catheter (not shown) to be directed within the patent's body, for example, intraarterially.

Figure 15:
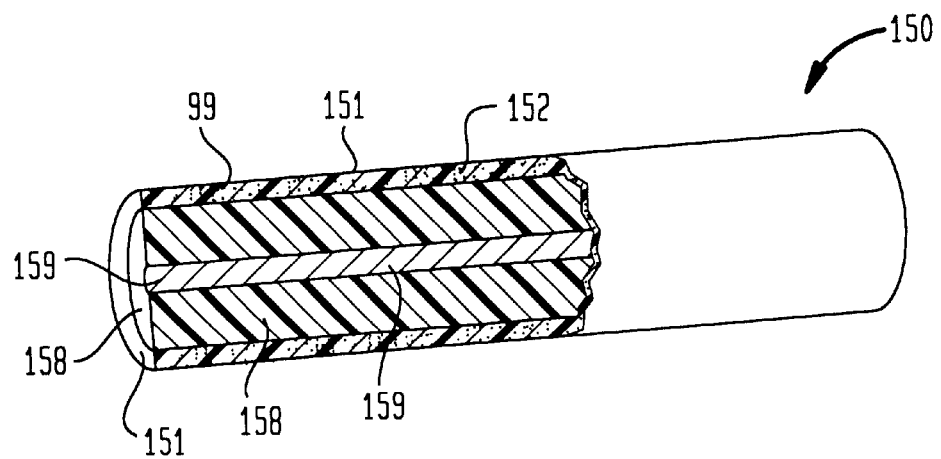
FIG. 15 is a partial cut-away perspective view showing an alternative embodiment to that of FIG. 14, wherein the metal wire does not extend beyond the end of the radioactive composite.

FIG. 15 shows a therapeutic source 150 formed of a tube of radioactive composite 99 which is similar to that shown in FIG. 14. Radioactive particles 152 are randomly dispersed in polymeric matrix material 151, and a nonradioactive core 158 of polymeric material extends therethrough similarly to that of element 148 of the embodiment of FIG. 14. A wire 159 extends axially through the core 158 in a manner similar to that of wire 129 in FIG. 12, for the same purpose as stated above.

Figure 16:
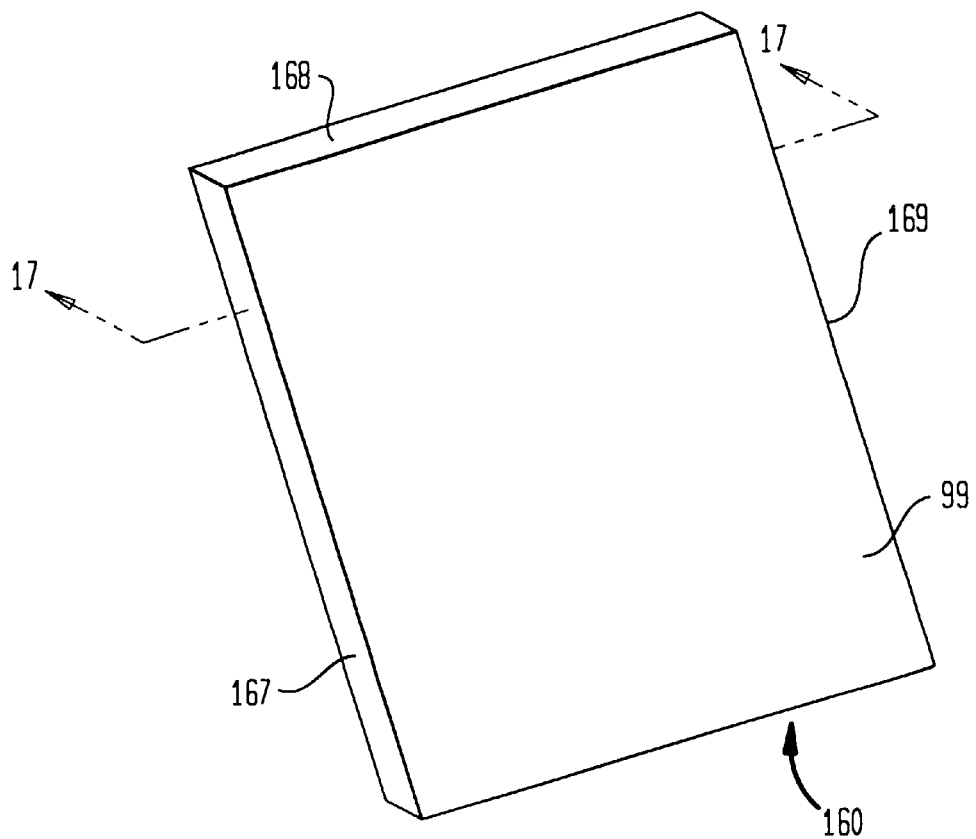
FIG. 16 is a perspective view of a radioactive composite of the present invention in the form of a sheet.
Figure 17:
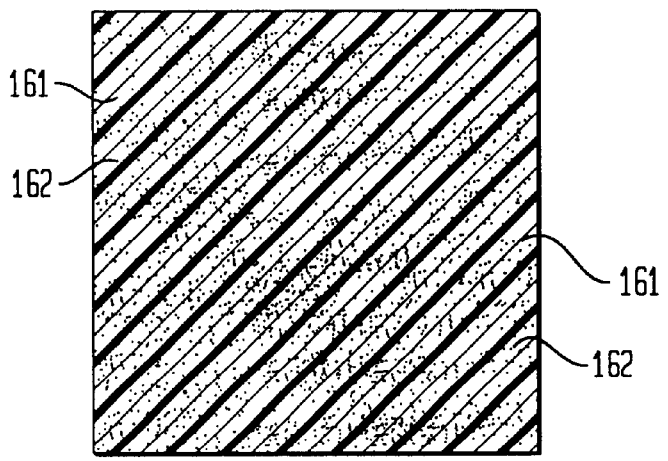
FIG. 17 is a sectional view of the embodiment of FIG. 15 taken through lines 17—17.

FIG. 16 shows a radioactive composite 160 in the form of a thick sheet of radioactive composite material 99 of the present invention. FIG. 17 shows a diagrammatic representation of a cross-section of the sheet 160, wherein polymeric matrix 161 is interspersed with randomly distributed fine radioactive particles 162.

The thickness of the radioactive composite 167 in this embodiment, can be varied to satisfy a particular need, but would typically range from 0.0005 to 0.3 mm. The length of the radioactive composite 169 can be any dimension desired and the width of the radioactive composite 168 can be from about 0.5 cm to 25 cm. Alternative embodiments include those that in addition to the radioactive composite material 99, have a polymeric or metal outer coating over the radioactive composite, thus forming a barrier to the leaching out of the radioactivity, and those which in addition or alternatively contain a radio-opaque wire through a portion or all of the length 169 or width 168 of the radioactive composite 99.

Figure 18:
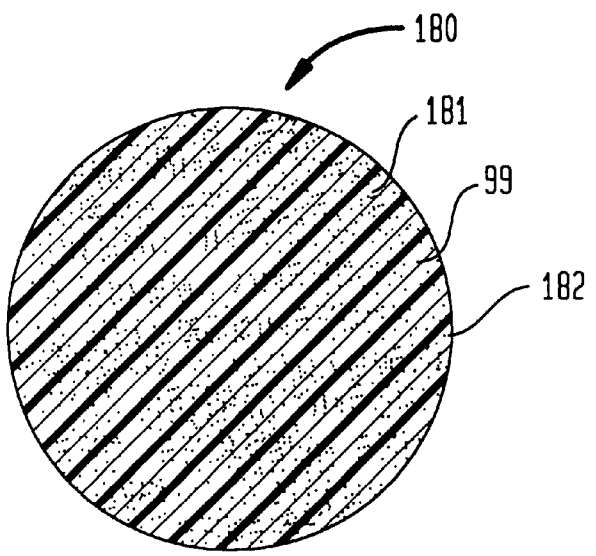
FIG. 18 is a sectional view of a microscopic spheroid of radioactive composite, in accordance with the invention.

FIG. 18 is a diagrammatic representation of a cross-section of a microscopic, essentially monodisperse spheroidal source 180 of radioactive composite 99, formed of polymeric matrix 181 and radioactive particles 182 randomly dispersed therethrough. The range for the mean of the diameter of the spheroidal sources is desirably from 10 to 100 microns, with the relative standard deviation around the mean being preferably no more than 10%. Such a monodisperse spherical source can be formed by extruding a monofilament and chopping it into uniform lengths such that the rod has a volume equivalent to the size sphere desired, followed by dropping the rods through a hot zone, containing if necessary a protective inert gas like dry nitrogen, at a high enough temperature to melt the polymer, thus forming a spherical particle. For example, to make 20-micron-diameter particles, a 20-micron rod can be cut into pieces 13 microns long. One modification to this embodiment includes a polymeric coating over the radioactive composite 99, thus forming a barrier to the leaching of radioactivity from the particles 182 dispersed in the polymeric matrix 181. Another alternative embodiment has, in addition, a metal sphere, e.g. formed by vapor deposition of titanium, that encapsulates the embodiment shown.

Figure 19:
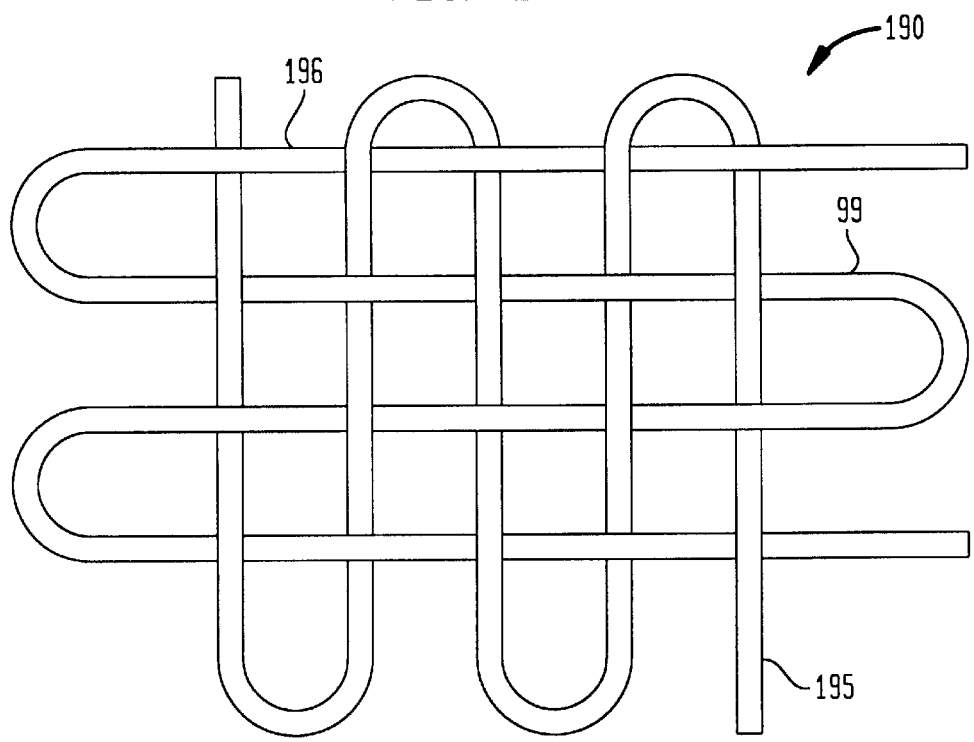
FIG. 19 is a plan view of a radioactive composite in the form of a warp and weft that have been entwined together to make a mesh, in accordance with the invention.

FIG. 19 diagrammatically represents a mesh of the present invention formed of radioactive composite 99, with flexible rod 195 interwoven with flexible rod 196 in the form of a warp and weft. As further illustrated by the drawing, the mesh can be prepared by a number of techniques producing a variety of patterns, depending upon that best suited for a particular application. The mesh can be fabricated by any of the multitude of commercial processes for weaving monofilament or multifilament thread into such a structure. The mesh can also be fabricated by the health care provider by utilizing a loom with pins positioned so as to provide a mesh with the correct number of monofilament lines per unit area, this number of monofilament lines being chosen based on the activity per unit length of mionofilament, so as to provide a desired therapeutic radiation dose upon implantation into diseased tissue. The most desirable shape for the mesh is determined by the application and the lesion of the particular patient involved.

Figure 20:
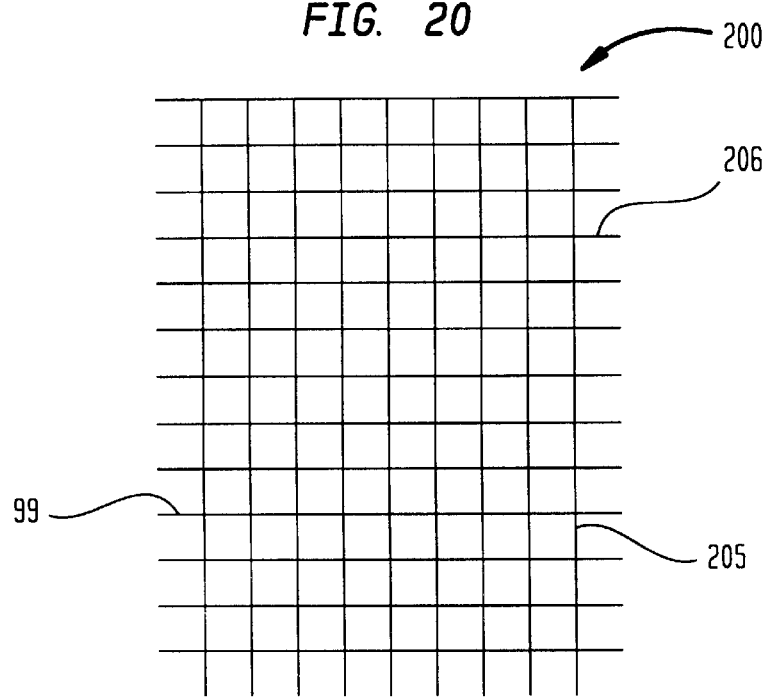
FIG. 20 is a diagrammatic plan view of a radioactive composite in the form of an alternative mesh embodying the invention.

FIG. 20 diagrammatically represents a mesh 200 of the present invention formed of radioactive composite 99. Where vertical rods 206 of composite 99 cross horizontal rods 206 of composite 99, they are cemented or otherwise joined at intersection points. A relatively rigid mesh 200 or sheet 160 may be formed into a size and shape which can be used to irradiate a bronchial tube, for example.

Figure 21:
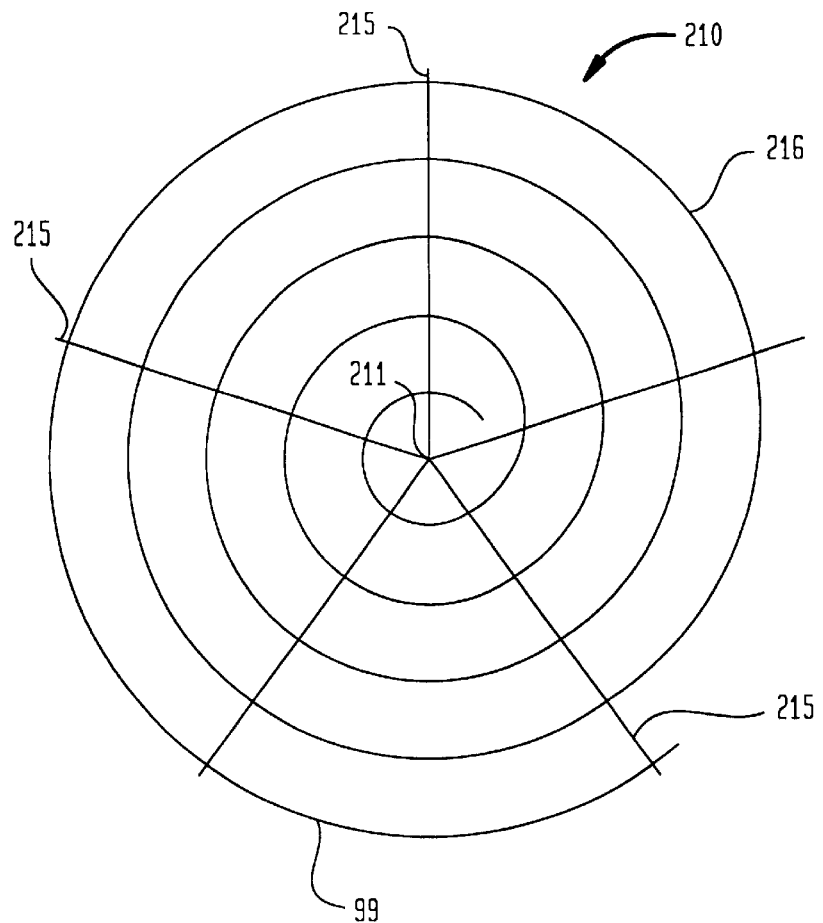
FIG. 21 is a diagrammatic plan view of a radioactive composite in the form of yet another alternative mesh embodying the invention.

FIG. 21 diagrammatically represents a spiral mesh 210 of the present invention formed of radioactive composite 99. Radial rods 215 are joined at a center joint 211, as by cement or ultrasonic welding. Where radial rods 215 intersect the spiral rod 216, they are similarly joined. The spiral mesh form 210 of radioactive composite may be useful in providing therapy to circular areas of the patient's body, for example, the eye.

Figure 22:
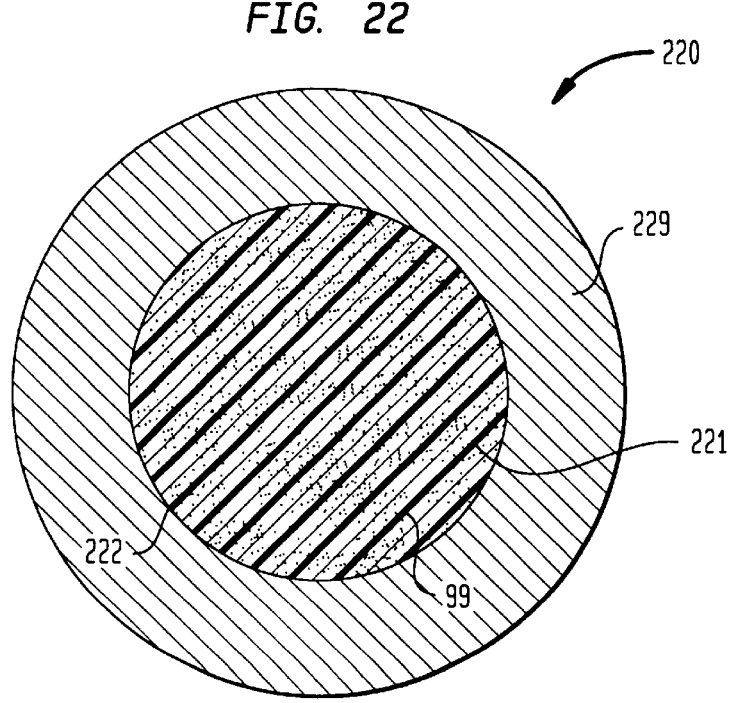
FIG. 22 is a cross-sectional view of a radioactive composite in the form of a right cylindrical rod encapsulated with a metal outer layer, in accordance with an embodiment of the invention

FIG. 22 diagrammatically represents the cross section of a therapeutic radiation source 220 of the present invention, in which a radioactive composite 99 having a polymeric matrix 221 through which are randomly dispersed radioactive particles 222 is disposed within a biocompatible metallic casing 229, for example titanium. As shown the casing 229 fits snugly about the polymeric matrix 221, but if desired for ease in fabrication, the diameter of the matrix 221 may be made smaller than the inner diameter of the casing 229.

Additional embodiments of the present invention include forming the radioactive composite by injection molding, blow molding or other appropriate process into shapes appropriate for use as intracavitary applicator therapeutic sources. The advantage of this type of therapeutic source is apparent in that the entire applicator body is radioactive so that the area treated receives a very uniform dose. Since the radiation emitted by the isotopes used can be shielded by a thin nontoxic material such as Lucite (polymethyl methacrylate) or leaded Lucite, the healthy tissue around the treatment volume can be effectively shielded. Such applicators are used in a variety of shapes and sizes making the use of the radioactive composite ideal for this application due to the simple molding procedures associated with plastic materials.

The present invention provides for the radioactive composite to be readily transformed into a multitude of shapes suitable for all forms of brachytherapeutic implants. In addition, although one aspect of the present invention is that the therapeutic source embodiments may be used in the absence of any encapsulation, still another aspect of the invention is the suitability of such a therapeutic source to be encapsulated in either radioactive or nonradioactive metallic or non-metallic capsules for use as brachytherapy sources.

Example 1

A therapeutic source is produced in the form of a right circular cylindrical rod, manufactured to have a preselected degree of flexibility, with a diameter of 0.8 mm, a selectable length and activity of 1 millicurie of Pd-103 per cm of length. The radioactive composite is prepared by first creating the Pd-103 activity required and then synthesizing the radioactive particulate.

The creation, separation and purification of the Pd-103 required is carried out according to the method of Carden as reported in U.S. Pat. No. 5,405,309. The essentially isotopically pure Pd-103 derived from the method of Carden is then added to the amount of palladium chloride required to form the desired mass of radioactive particulate. For example, if 30 Curie of Pd-103 is introduced into the process, and a specific activity of 60 Curies per gram is desired, 0.50 grams of palladium must be supplied in the palladium chloride since the palladium mass associated with the Pd-103 is negligible. If the activity desired on the first day of sale is 1 millicurie per cm and 7 days are required for manufacturing and shipping between shutting down the cyclotron and the day of first sale, then 30 Ci of initial activity is required to yield 22.5 Ci on that day of first sale. In addition, some self-absorption in the palladium particles and some bulk absorption in the polymer and neighboring palladium particles will occur, resulting in an apparent loss of approximately 6% of the activity, thus providing an effective activity of 21 Ci on the first day of sale. Finally, an additional 5% of the activity is actually lost in processing, leaving a final apparent activity of 20 Ci on the first day of sale.

Since the desired source strength is 1 mCi per cm, approximately 20,000 cm of rod can be produced. Since the density of palladium is approximately 12 g per ml, the total volume of palladium metal being added to the polymer is approximately 0.04 ml. The volume per cm of rod is approximately 0.005 ml. Thus the volume of polymer is approximately 100 ml, resulting in a metal loading of approximately 0.04% by volume. The total metal volume per cm of rod is approximately $2.0 \times 10^{-6}$ ml.

Particles are then prepared from the palladium chloride solution above by the method of Boutonnet et. al. (Boutonnet, M., Kizling, J. and Stenius, P., "The Preparation of Monodisperse Colloidal Particles from Microemulsions," Colloids and Surfaces, 5, 209–225, 1982) This procedure can, for example, be practiced by dissolving the 0.5 g of palladium chloride and Pd-103 chloride in the hexane, PEGDE (pentaethyleneglycol dodecyl ether), water microemulsion system of Boutonnet and reducing by adding hydrazine (2% by volume) at 30 degrees centigrade for approximately 30 minutes. The palladium-103 chloride is derived from the amine complex resulting from the Carden procedure by 3 evaporations of the Pd-103 amine complex dissolved in concentrated hydrochloric acid. This procedure results in a stable emulsion of hexane and very small particles, approximately 50 Angstroms in diameter with a relative standard deviation in the mean diameter of approximately 10%. The emulsion is essentially hexane, approximately 75%.

The radioactive composite can now be compounded by introducing the desired polymer, in this case polyurethane. Commercial polyurethane resin is used, with the grade chosen to provide the degree of flexibility desired. For example, B. F. Goodrich's Estane. (thermoplastic polyurethane) type 58271 has a stiffness modulus of 3,000 psi while type 58137 has a stiffness modulus of 30,000 psi at 23 degrees centigrade.

Prior to mixing, the radioactive particulate is in a hexane solution of approximately 1 liter volume, and approximately 100 ml of polymer resin is required. The radioactive particulate can be mixed with the resin by tumbling the resin with the slow addition of the hexane solution to allow solvent evaporation. Alternatively mixing can be accomplished by adding the hexane solution into the extrusion feed screw as the plastic is being extruded. Standard extrusion technology (with concomitant heating) can be used, with the exception that the resin before extrusion should be very dry to avoid degradation during extrusion, and extruded materials should be kept dry in case chopping and reextrusion is required.

The activity per unit length of the rod can be measured by feeding the rod under a sodium iodide detector. If the observed value is too high, the extruded rod can be chopped, its dryness ensured, and reextruded to provide the desired activity per unit length.

Example 2

A therapeutic source in the form of a sheet or film can be fabricated from the radioactive composite by extrusion. A procedure for carrying out this fabrication involves first preparing a rod as in Example 1 such that the activity per unit volume of the rod will, when extruded into a sheet or film provide the activity per unit area of film desired. For example, if a film 0.03 mm in thickness with an activity of 1 mCi per square centimeter on the first day of delivery is desired, rod must be prepared as above containing 1 mCi in 0.003 ml of rod or about 1.7 mCi per cm of rod. The film is then prepared from the rod by chopping the rod into short pellets, carefully drying the pellets, adding any additional polymer required to obtain the desired activity and extruding the plastic by normal techniques.

Example 3

A therapeutic source in the form of a 0.8 mm rod is prepared as described in Example 1, above. Rod with an activity of 1 mCi per cm having a coaxial radiopaque gold wire can be fabricated from the radioactive composite by a standard extrusion process utilizing a cross head wire coating die. The radioactive composite is prepared by the method outlined in Example 1 above except that the additional bulk absorption occurring in the wire must be overcome by adding an additional 5% activity to the radioactive composite.

Example 4

The rod of Example 1, when extruded from a polymer with the appropriate flexibility, can be used to form a radioactive mesh by either weaving the mesh from the rods (i.e. sutures) as in FIG. 19 or by laying one layer of evenly spaced rods on top of another but with the rod directions for the two layers perpendicular and the points of contact between the two layers of rods being bonded by adhesive as in FIG. 20. Such a mesh, if rod spacing is 1 cm in each direction, will have 2 mCi of radioactivity per square cm of mesh. The activity of the mesh can be adjusted by adjusting the tightness of the weave, i.e., the space between rods. The activity of the mesh per unit area varies as the inverse of the square of the distance between rods. For example, if the mesh spacing in this example is changed to 0.5 cm in each direction, then the mesh will have a radioactivity of 8 mCi per square cm.

It should be understood that the detailed description and examples presented above are for purposes of illustration. Other embodiments which employ the principles of the invention and fall with in the spirit and scope thereof will be apparent from the present disclosure to those skilled in the art. For example, the polymeric matrix may be synthesized by polymerization in the presence the radioactive powder.

TABLE 1

ACCEPTABLE NONABSORBABLE POLYMERS WITH THEIR TRADE NAMES AND COMMERCIAL SOURCES

| Material | Trade Names | Sources |
| --- | --- | --- |
| Polyurethane | Texin, Desmopan, Estane | Bayer Corp., B F Goodrich |
| Polypropylene | Surgilene, Prolene | Ethicon, American Cyanamid |
| Polyethylene terephthalate (PET) | Impet, Petra, Rynite, Estar | Allied, Hoechst, Celanese, duPont, Eastman |
| Polyphenylene oxide blends (PPO) | Noryl, Prevex | General Electric |
| Polyphenylsulfone (PPSU) | Radel R | Amoco |
| Polysulfone (PSU) | Udel, Ultrason S | Amoco, BASF |
| Polyether sulfone (PES) | Radel A, Ultrason E | Amoco, BASF |
| Polyphenylene sulfide (PPS) | Fortron, Ryton, Supec | Hoechst, Celanese, Phillips, GE |
| Phenyletheretherketone (PEEK) | Kadel, Victrex | Amoco, Victrex |
| Polyetherimide (PEI) | Ultem | GE |
| Silicone | Silastic | Dow Corning |
| Liquid crystal polymer (LCP) | Vectra | Hoechst, Celanese |

TABLE 2

ACCEPTABLE ABSORBABLE POLYMERS WITH THEIR TRADE NAMES, TIME TO TOTAL ABSORPTION AND COMMERCIAL SOURCES

| Material, Trade Name | Days to Total Absorption | Commercial Sources |
|---|---|---|
| Polyglycaprone 25, Moncryl | 100 | Ethicon, Inc. |
| Polyglactin 910, Vicryl | 63 | Ethicon, Inc. |
| Polydioanone, PDS II | 180 | Ethicon, Inc. |

We claim:

1. A therapeutic source comprising a radioactive composite consisting essentially of (a) a polymeric matrix and (b) a radioactive powder consisting essentially of microscopic radioactive particles at least 0.002 micron in average dimension randomly and essentially uniformly dispersed within said polymeric matrix;

wherein said polymeric matrix is a biocompatible polymer.

2. A therapeutic source of claim 1, wherein the polymer is selected from the group consisting of polyurethane, polyethylene terephthalate, polyphenylene oxide blends, polyphenylsulfone, polysulfone, polyether sulfone, polyphenylene sulfide, phenyletheretherketone, polyetherimide, liquid crystal polymer and silicone.

3. A therapeutic source of claim 1, adapted to be implanted in the body of a patient and to disintegrate after a predetermined period.

4. A therapeutic source of claim 3, wherein the predetermined period to disintegrate is adapted to be at least ten times the half-life of the radioactive powder.

5. A therapeutic source of claim 3, wherein the polymer is selected from the group consisting of polyglycaprone 25, polyglactin 910 and polydioanone.

6. A therapeutic source of claim 1, having a shape selected from the group consisting of a structure that is solid in cross section; a structure that is hollow in cross section; a suture; a mesh; a film; a sheet; and a multiplicity of microscopic essentially monodisperse spheroidal sources.

7. A therapeutic source of claim 1, having a shape selected from the group consisting of a structure that is solid in cross section; a structure that is hollow in cross section; a suture; a mesh; a film; and a sheet; and further comprising a radiographically detectable element for locating the source within the body of a patient.

8. A therapeutic source of claim 1, wherein the radioactive composite is in the shape of a right circular cylindrical rod, solid in cross section, having a cylindrical wall and a pair of ends on opposite sides thereof, and wherein the therapeutic source further comprises a non-radioactive sleeve which surrounds the cylindrical wall.

9. A therapeutic source of claim 8, further comprising a pair of caps covering said ends of the radioactive composite.

10. A therapeutic source of claim 8, further comprising a radiographically detectable element for locating the source within the body of a patient.

11. A therapeutic source of claim 8, further comprising an axial wire having a tail portion that extends beyond an end of the radioactive composite, whereby said tail portion is adapted to be secured to a catheter.

12. A therapeutic source of claim 1, wherein the radioactive composite is in the shape of a right circular cylindrical rod, hollow in cross section, and having a cylindrical wall and a pair of ends on opposite sides thereof.

13. A therapeutic source of claim 12, further comprising a non-radioactive polymeric core that extends axially through the radioactive composite.

14. A therapeutic source of claim 13, further comprising a radiographically detectable element for locating the source within the body of a patient.

15. A therapeutic source of claim 13, further comprising an axial wire having a tail portion that extends beyond an end of the radioactive composite, whereby said tail portion is adapted to be secured to a catheter.

16. A therapeutic source of claim 1, wherein the radioactive composite is in the shape of a mesh comprising vertical and horizontal rods that cross at intersection points.

17. A therapeutic source of claim 1, wherein the radioactive composite is in the shape of a spiral mesh.

18. A therapeutic source comprising a radioactive composite of claim 6, wherein the radioactive composite is formed as a multiplicity of microscopic, essentially monodisperse spheroidal sources, further comprising a biocompatible spheroidal casing surrounding each of said spheroidal sources.

19. A therapeutic source of claim 1, wherein said microscopic radioactive particles are of essentially uniform average dimension and wherein said average dimension is in the range from 0.002 micron to 20 microns.

20. A therapeutic source of claim 19, wherein the very fine radioactive particles are an yttrium oxide ceramic.

21. A method of making a therapeutic source of claim 1, comprising the steps of:

(a) mixing a radioactive powder dispersed in a solvent, with a biocompatible polymer;

(b) removing the solvent to form a mixture;

(c) extruding the mixture to form an extruded mixture; and (d) cutting said extruded mixture to form said therapeutic source;

whereby said therapeutic source is adapted to deliver a therapeutic dose of radiation.

22. The method of claim 21, wherein the solvent is hexane and the radioactive powder comprises palladium-103.

23. A method of using the therapeutic source of claim 1 for delivering a therapeutic dose of radiation to a diseased tissue in a patient comprising the steps of:

(a) compounding said radioactive composite to form a compounded flexible radioactive composite;

(b) forming said compounded flexible radioactive composite into one or more devices having a solid or hollow generally cylindrical shape;

(c) cutting said devices into sizes that together provide therapeutic sources adapted for delivery of a therapeutic dose of radiation to said diseased tissue; and (d) placing said cut devices in positions so as to irradiate the diseased tissue.

24. A method of claim 23, wherein the placing step (d) comprises placing said therapeutic source with an intracavitary or intralumenal applicator for delivering a radiation dose into the cavity to treat diseased tissue in close proximity to the cavity.

25. A method of using the therapeutic source of claim 1 for delivering a therapeutic dose of radiation to a diseased tissue in a patient comprising the steps of:

(a) compounding said radioactive composite to form a compounded flexible radioactive composite;

(b) fashioning said compounded flexible radioactive composite into a therapeutic source adapted to deliver a therapeutic dose of radiation to a diseased tissue; and (c) placing said therapeutic source with the diseased tissue.

26. A method of claim 25, wherein the therapeutic source is a hollow cylinder, and wherein the placing step(c) comprises threading said therapeutic source onto a catheter and using the catheter to place said therapeutic source within vascular tissue in a position and for a time sufficient to prevent restenosis in the irradiated area of the vessel.

27. A method of claim 25, wherein the therapeutic source is formed with a radiographically detectable element, further comprising the step of visualizing the radiographically detectable element with medical X-ray equipment, whereby the position of the therapeutic source with respect to the diseased tissue is determined.

28. A method of claim 25, wherein said therapeutic source is adapted to disintegrate in the living body of the patient over a defined time period, whereby said therapeutic source delivers a therapeutic dose of radiation and then disintegrates.

29. A method of claim 25, wherein said therapeutic source is a flexible suture and wherein step (c) is accomplished by sewing the flexible suture into the diseased tissue.

30. A method of claim 25, wherein said therapeutic source is a sheet and step (b) is accomplished by fashioning the sheet with a thickness and dimension selected to provide appropriate irradiation to the diseased tissue.

31. A method of claim 30, wherein step (c) comprises incorporating said sheet into an intracavitary or intraluminal applicator intended to deliver a therapeutic dose of radiation to diseased tissue surrounding the applicator, and further comprising the step of (d) implanting an intracavitary or intraluminal applicator into the diseased tissue.

32. A therapeutic source of claim 1, wherein said radioactive powder comprises a radioisotope selected from the group consisting of palladium-103, yttrium-90, phosphorus-32, and gold-198.

33. A therapeutic source of claim 10, wherein said radioactive powder comprises palladium-103.

34. A therapeutic source of claim 10, wherein said biocompatible polymer is polyurethane.

35. A therapeutic source of claim 1, adapted to be stable within the body of a patient.

36. A therapeutic source of claim 19, wherein the microscopic radioactive particles comprise a radioisotope surrounded by a layer of a material selected from the group consisting of titanium, platinum, gold, and graphite.

* * * * *

UNITED STATES PATENT AND TRADEMARK OFFICE
CERTIFICATE OF CORRECTION

PATENT NO. : 6,589,502 B1
DATED : July 8, 2003
INVENTOR(S) : Coniglione et al.

It is certified that error appears in the above-identified patent and that said Letters Patent is hereby corrected as shown below:

Title page,
Item [*] Notice, "Subject to any disclaimer, the term of this patent is extended or adjusted under 35 U.S.C. 154(b) by 0 days." should read -- Subject to any disclaimer, the term of this patent is extended or adjusted under 35 U.S.C. 154(b) by 1572 days. --.

Signed and Sealed this

Twenty-eighth Day of February, 2006

JON W. DUDAS
*Director of the United States Patent and Trademark Office*